(12) United States Patent
Noda et al.

(10) Patent No.: US 8,105,264 B2
(45) Date of Patent: *Jan. 31, 2012

(54) INDWELLING HEAT EXCHANGE CATHETER AND METHOD OF USING SAME

(75) Inventors: Wayne A. Noda, Mission Viejo, CA (US); Mike L. Jones, Capistrano Beach, CA (US); Scott M. Evans, Santa Ana, CA (US); Blair D. Walker, Mission Viejo, CA (US); William J. Worchen, Coto de Caza, CA (US); Yves Pierre Gobin, Los Angeles, CA (US)

(73) Assignees: Zoll Circulation, Inc., Sunnyvale, CA (US); The Regents of the University of Califonia, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/021,559

(22) Filed: Feb. 4, 2011

(65) Prior Publication Data

US 2011/0130812 A1    Jun. 2, 2011

Related U.S. Application Data

(63) Continuation of application No. 12/794,924, filed on Jun. 7, 2010, which is a continuation of application No. 11/129,980, filed on May 16, 2005, now Pat. No. 7,857,781, which is a continuation of application No. 09/946,835, filed on Sep. 4, 2001, now Pat. No. 6,893,419, which is a continuation of application No. 09/133,813, filed on Aug. 13, 1998, now Pat. No. 6,338,727, which is a continuation-in-part of application No. 09/063,984, filed on Apr. 21, 1998, now Pat. No. 6,126,684.

(51) Int. Cl.
*A61M 37/00* (2006.01)

(52) U.S. Cl. .......... 604/6.13; 604/95.03; 604/96.01; 604/101.01; 604/101.03; 604/101.05; 604/102.01; 604/102.02; 604/102.03; 604/103.07; 604/113; 604/43; 604/23; 604/104; 604/105; 604/106; 604/114; 604/264; 604/291; 604/523; 606/20; 606/21; 606/22; 606/23; 606/24; 606/25; 606/26; 606/27; 606/28; 607/113; 607/105; 607/106; 607/108; 607/104; 607/109; 607/110; 607/111; 607/112; 607/114; 607/96; 128/898

(58) Field of Classification Search .......... 604/95.03, 604/96.01, 101.01, 101.03, 101.05, 102.01, 604/102.02, 102.03, 103.07, 113, 43, 23, 604/104–106, 114, 264, 291, 523; 606/20–28; 607/96, 104–106, 108–114; 128/898
See application file for complete search history.

(56) References Cited

U.S. PATENT DOCUMENTS 4,581,017 A * 4/1986 Sahota .......... 604/101.01
(Continued)

*Primary Examiner* — Tatyana Zalukaeva
*Assistant Examiner* — Ginger T Chapman
(74) *Attorney, Agent, or Firm* — John L. Rogitz

(57) ABSTRACT

A catheter is adapted to exchange heat with a body fluid, such as blood, flowing in a body conduit, such as a blood vessel. The catheter includes a shaft with a heat exchange region disposed at its distal end. This region may include hollow fibers which are adapted to receive a remotely cooled heat exchange fluid preferably flowing in a direction counter to that of the body fluid. The hollow fibers enhance the surface area of contact, as well as the mixing of both the heat exchange fluid and the body fluid. The catheter can be positioned to produce hypothermia in a selective area of the body or alternatively positioned to systemically cool the entire body system.

35 Claims, 19 Drawing Sheets

U.S. PATENT DOCUMENTS

| | | | | |
|---|---|---|---|---|
| 4,787,388 A | * | 11/1988 | Hofmann | 606/194 |
| 4,906,237 A | * | 3/1990 | Johansson et al. | 604/265 |
| 5,383,856 A | * | 1/1995 | Bersin | 604/101.01 |
| 5,486,208 A | * | 1/1996 | Ginsburg | 607/106 |
| 5,837,003 A | * | 11/1998 | Ginsburg | 607/106 |
| 5,957,963 A | * | 9/1999 | Dobak, III | 607/104 |
| 6,051,019 A | * | 4/2000 | Dobak, III | 607/104 |
| 6,126,684 A | * | 10/2000 | Gobin et al. | 607/113 |
| 6,283,940 B1 | * | 9/2001 | Mulholland | 604/96.01 |
| 6,338,727 B1 | * | 1/2002 | Noda et al. | 604/113 |
| 6,893,419 B2 | * | 5/2005 | Noda et al. | 604/113 |
| 7,857,781 B2 | * | 12/2010 | Noda et al. | 604/6.13 |

* cited by examiner

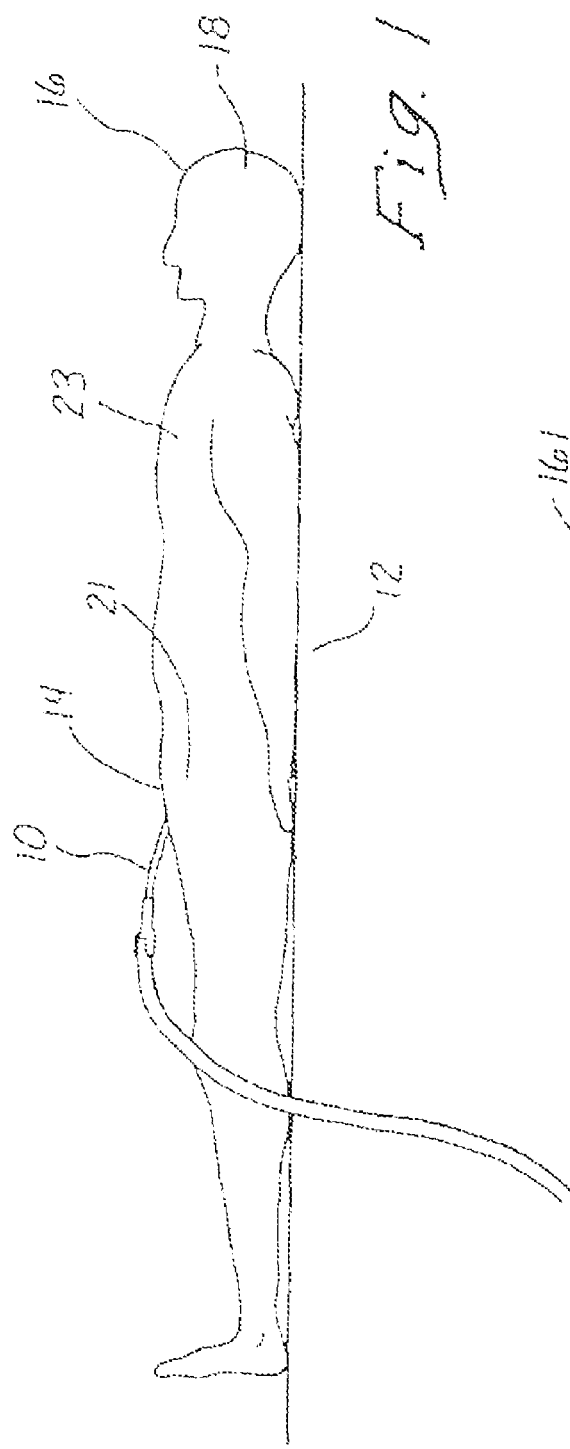
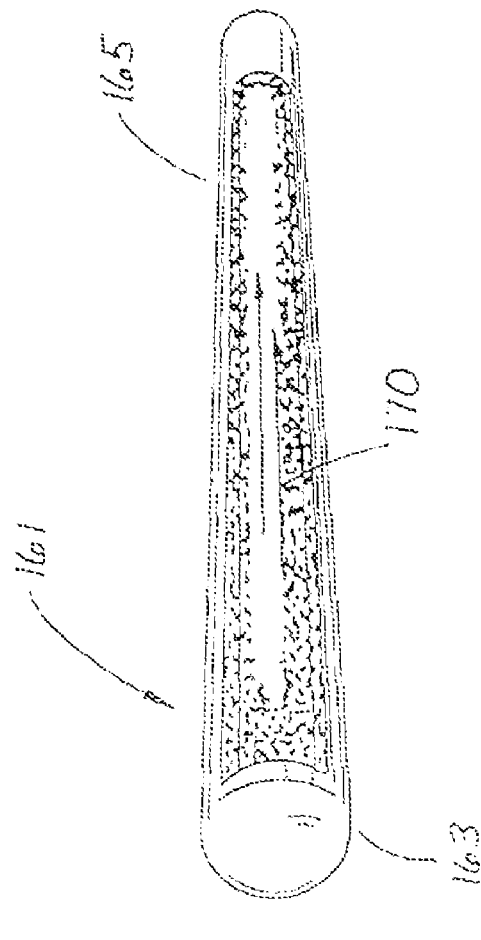

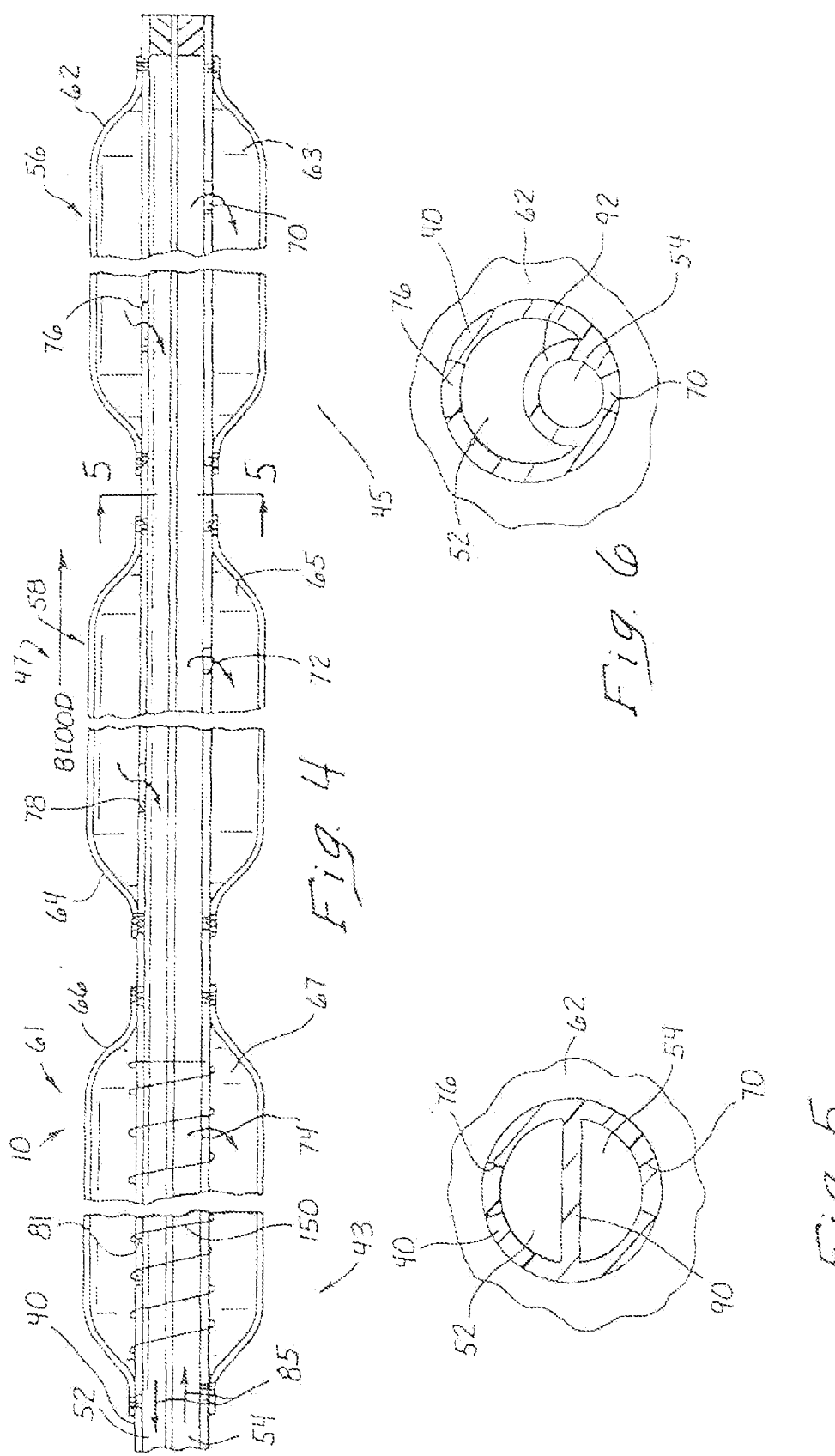

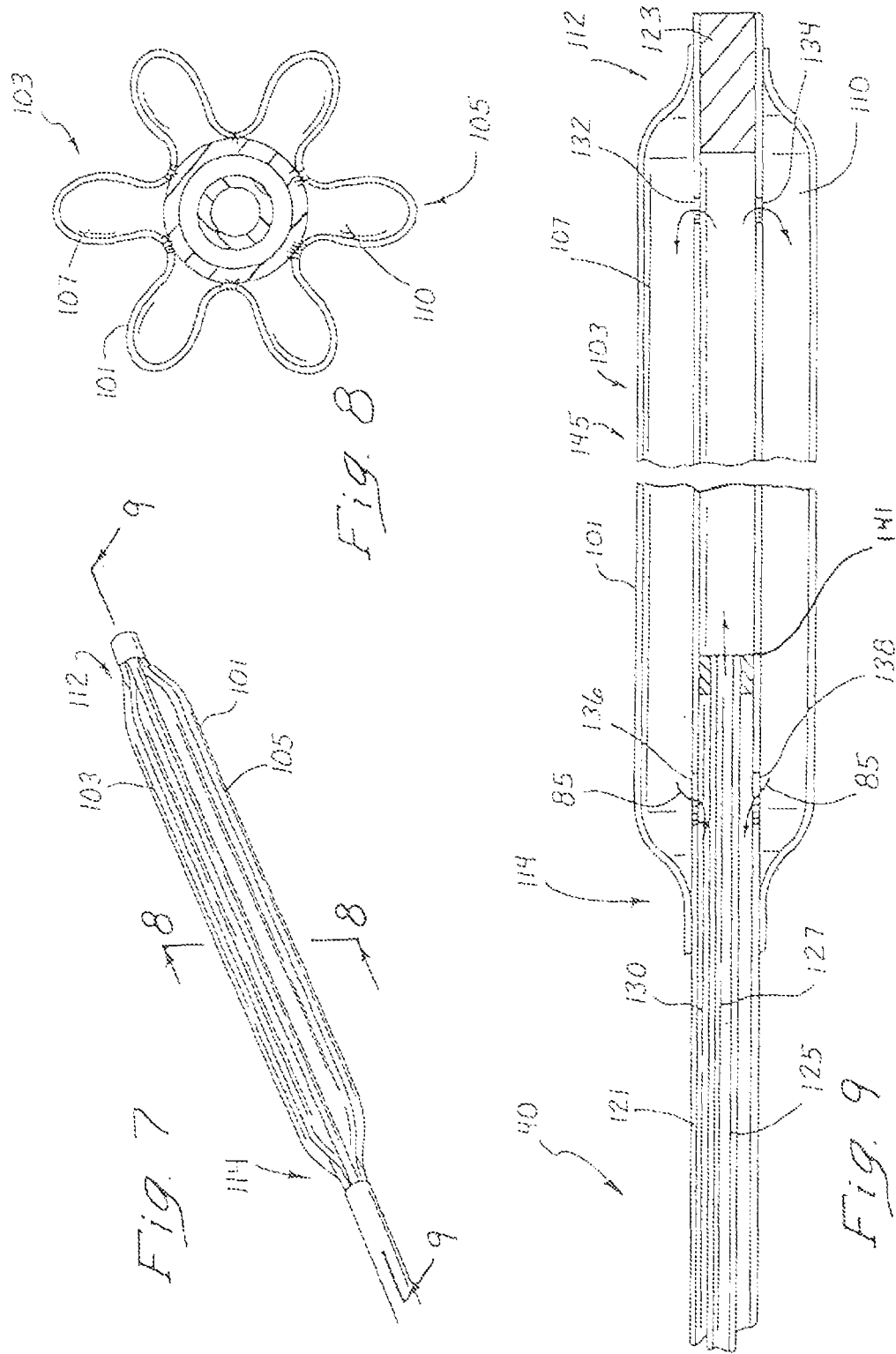

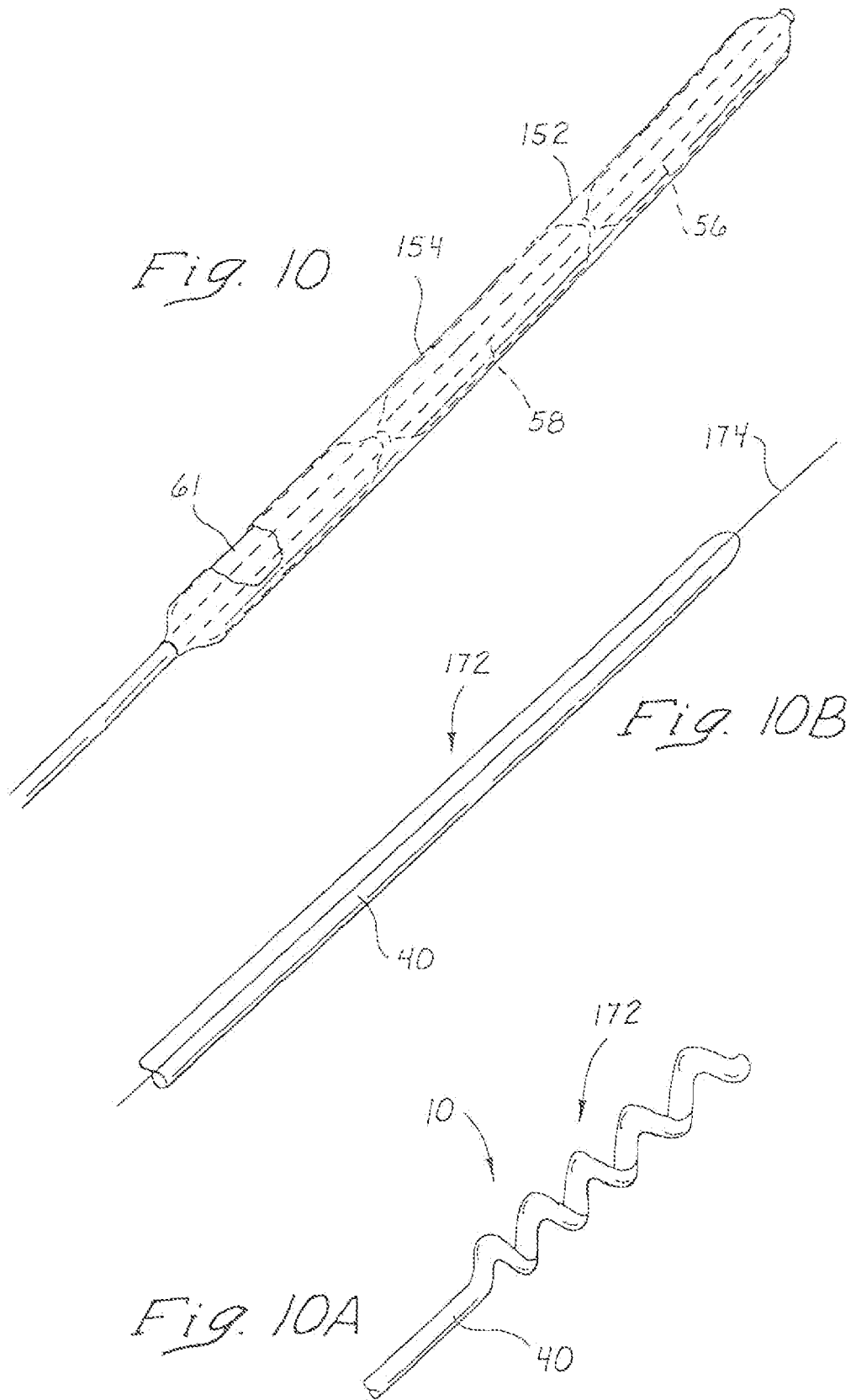

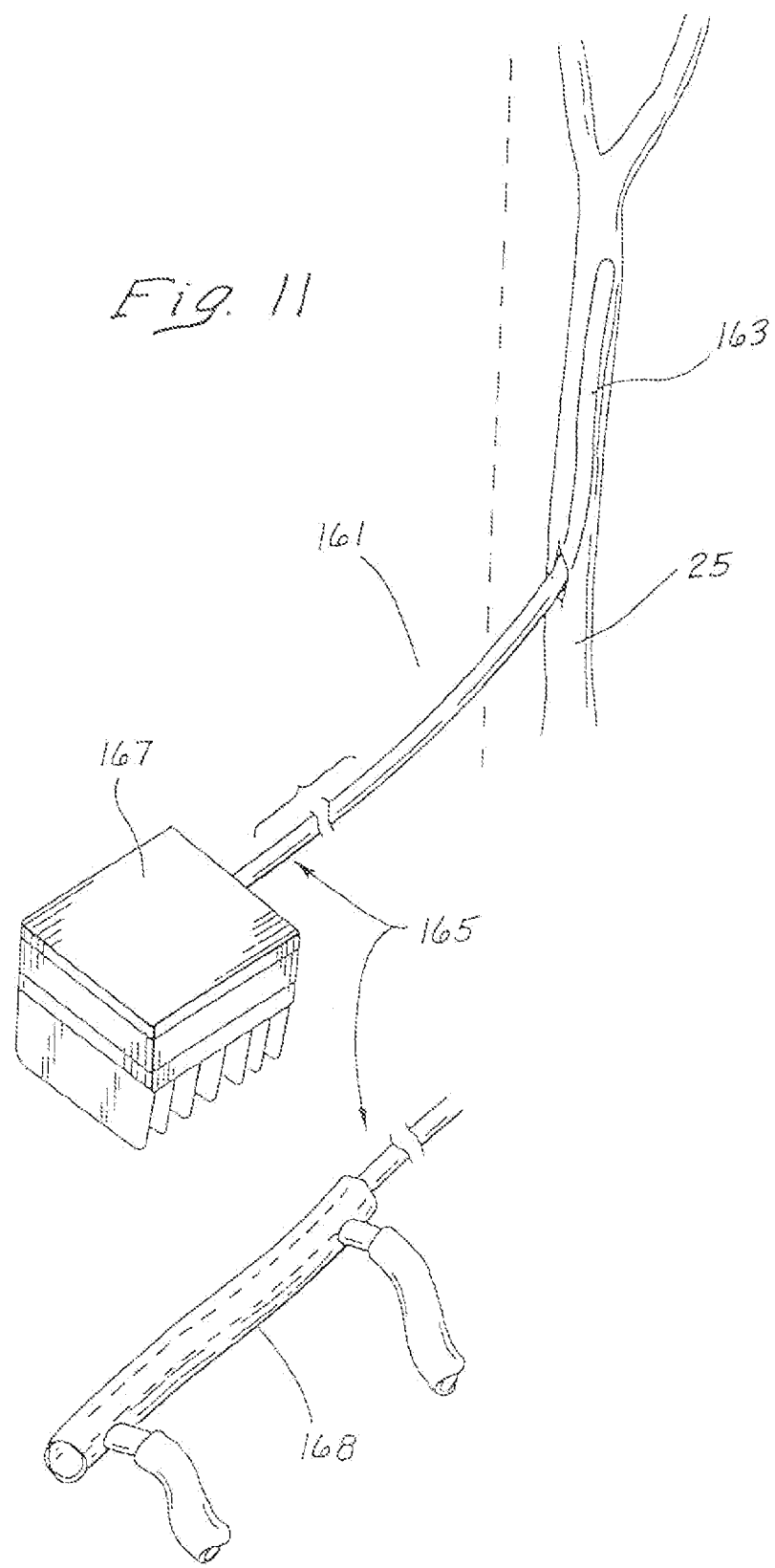

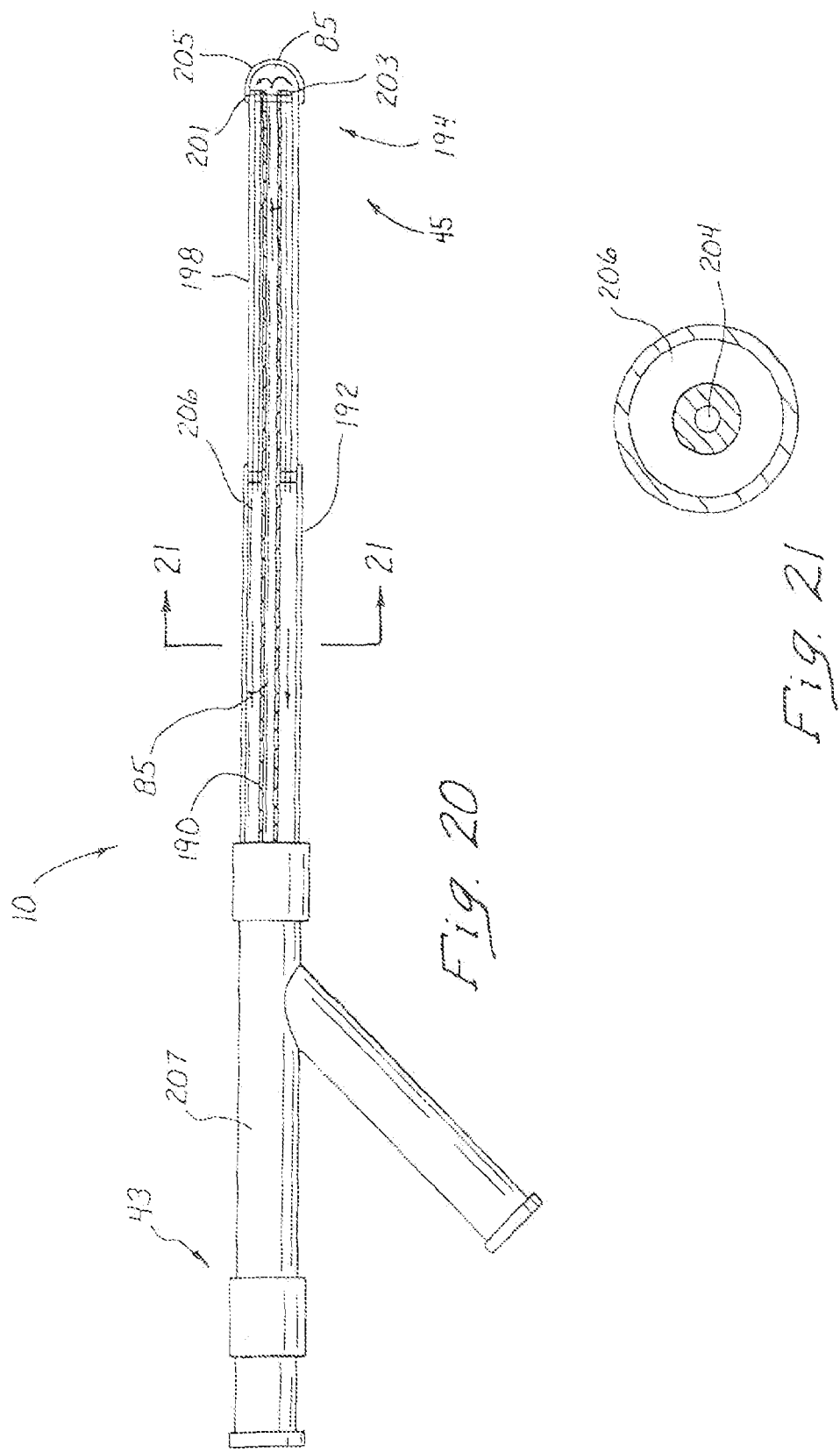

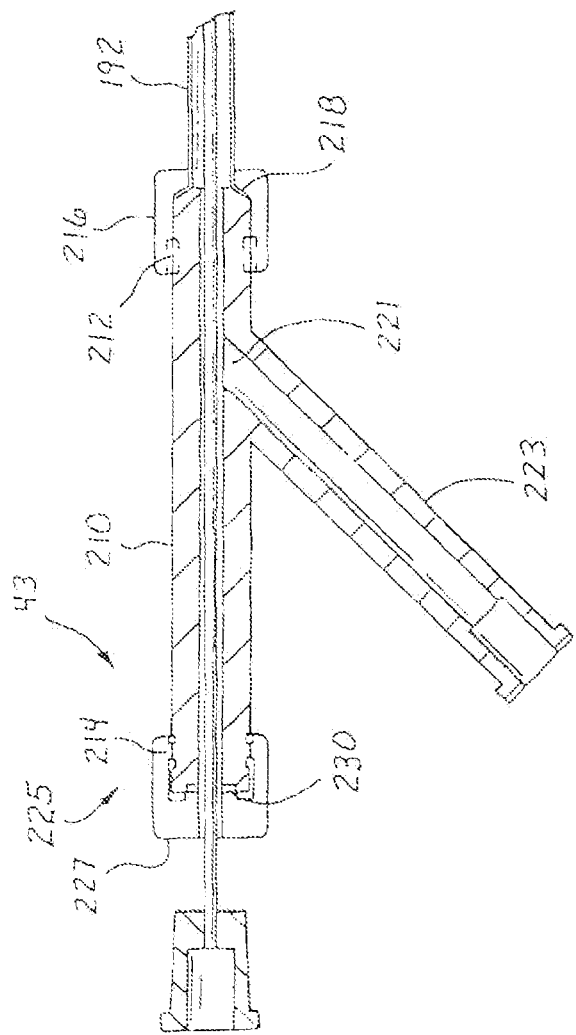
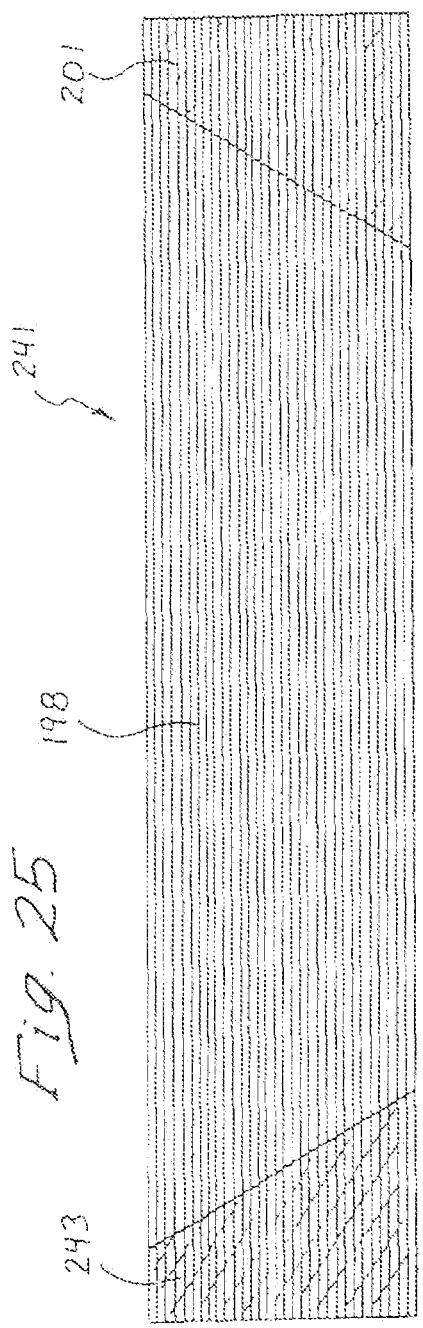

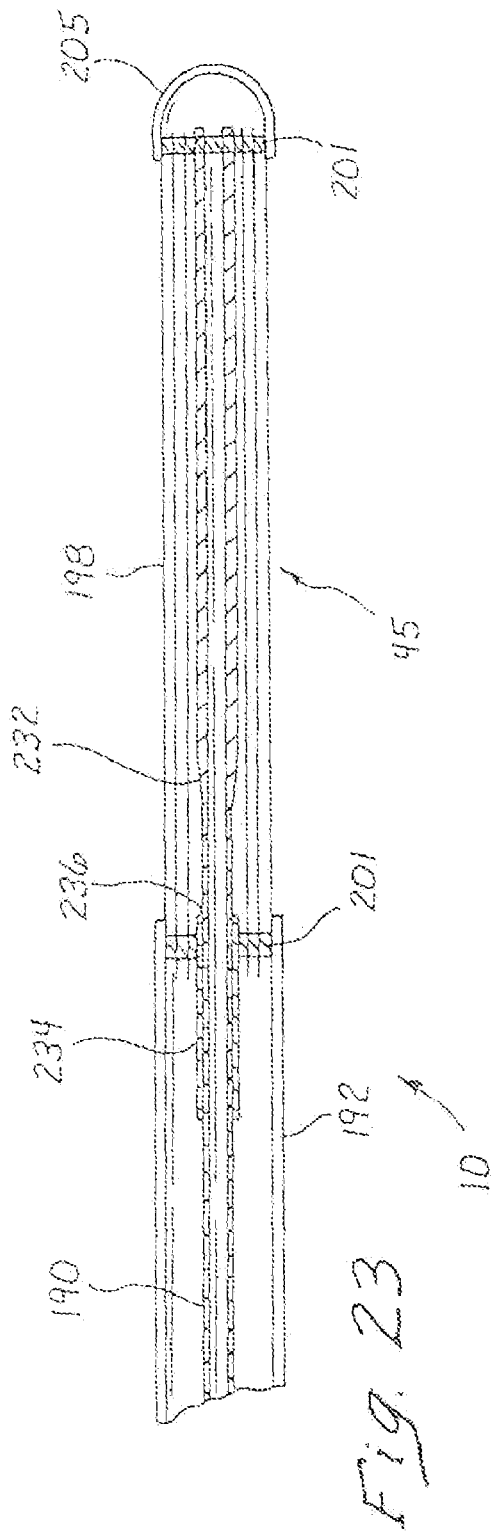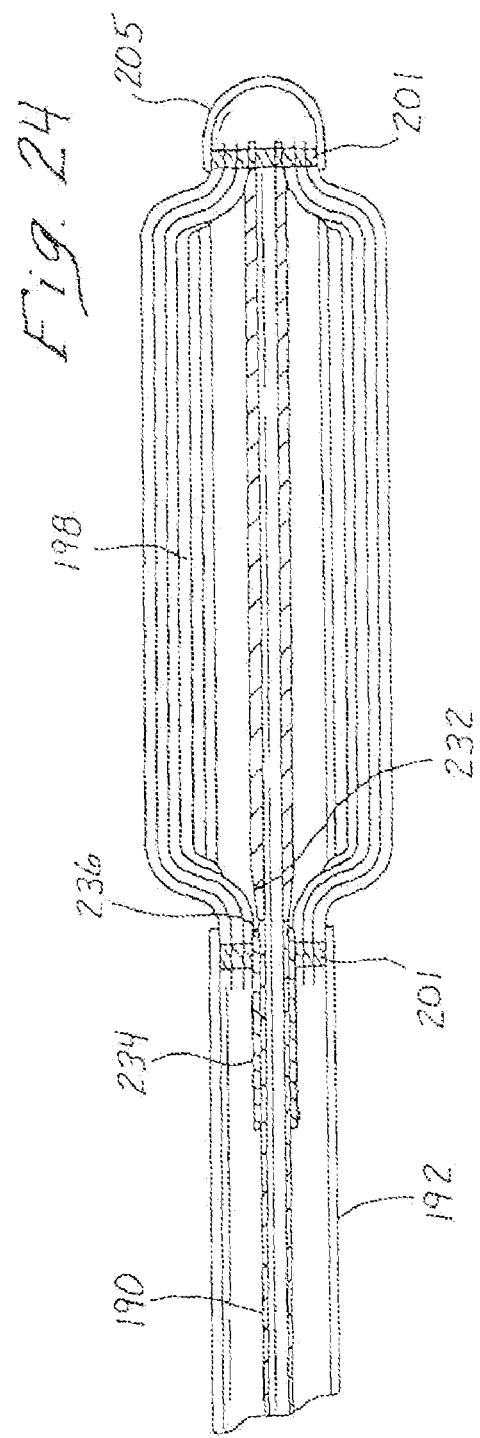

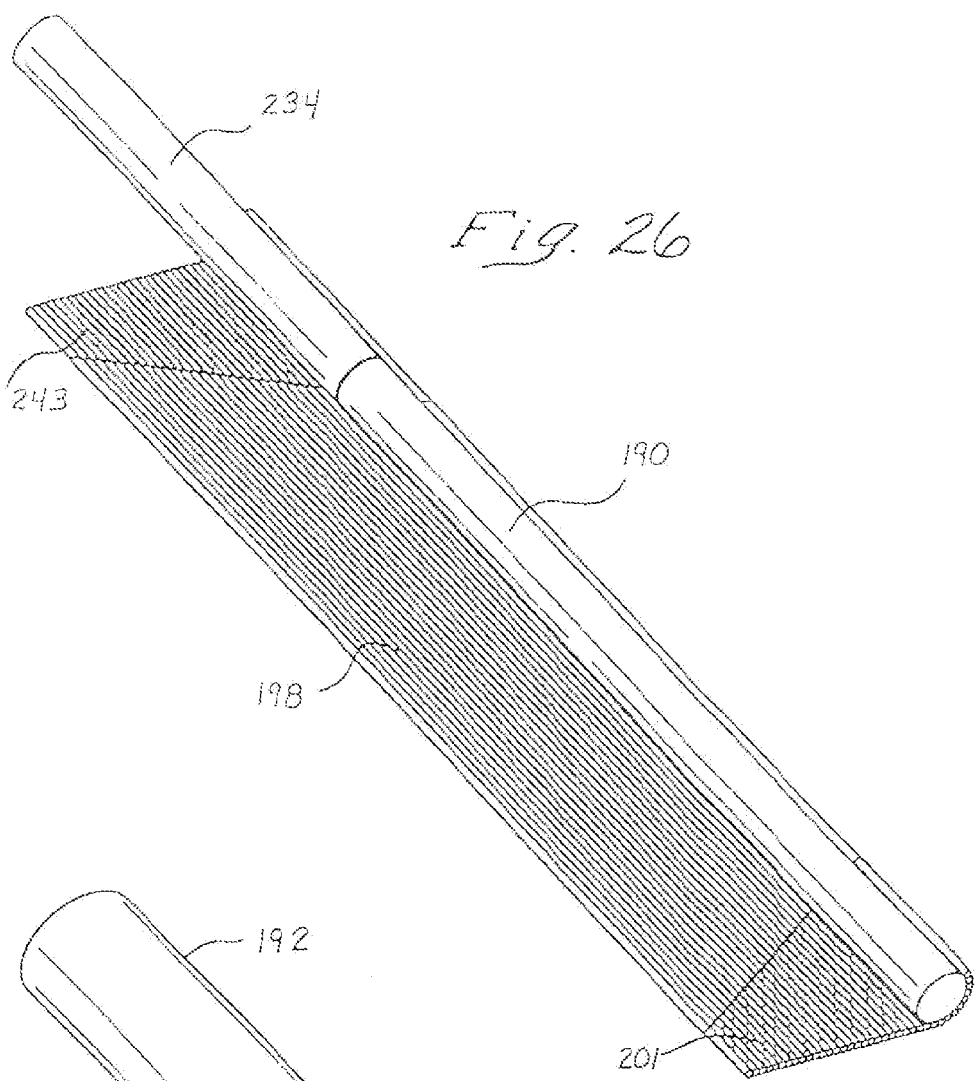
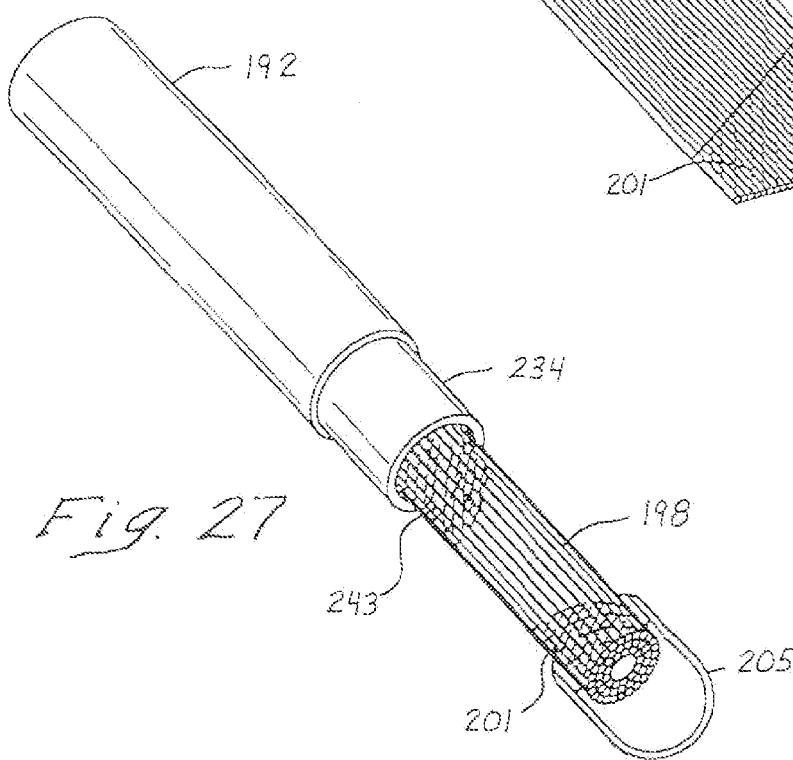

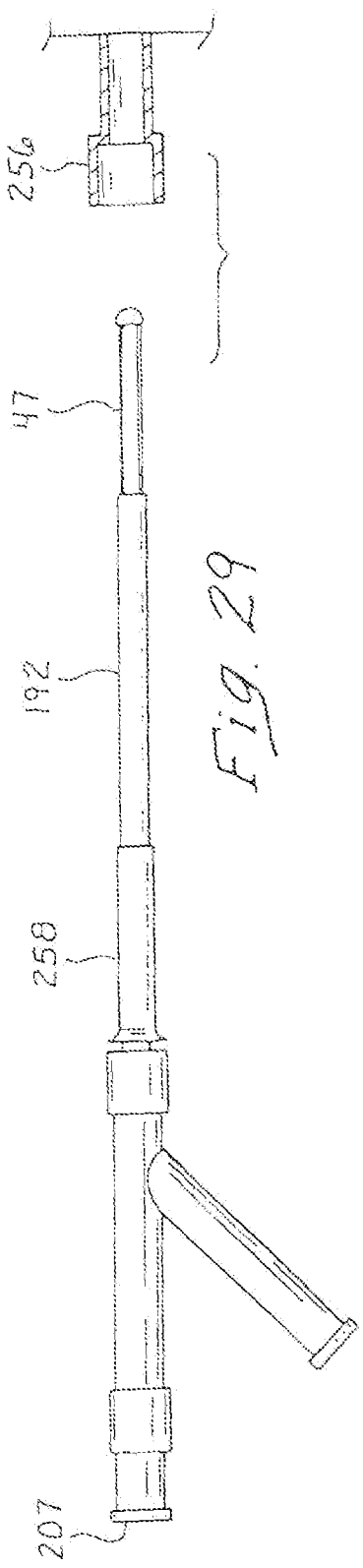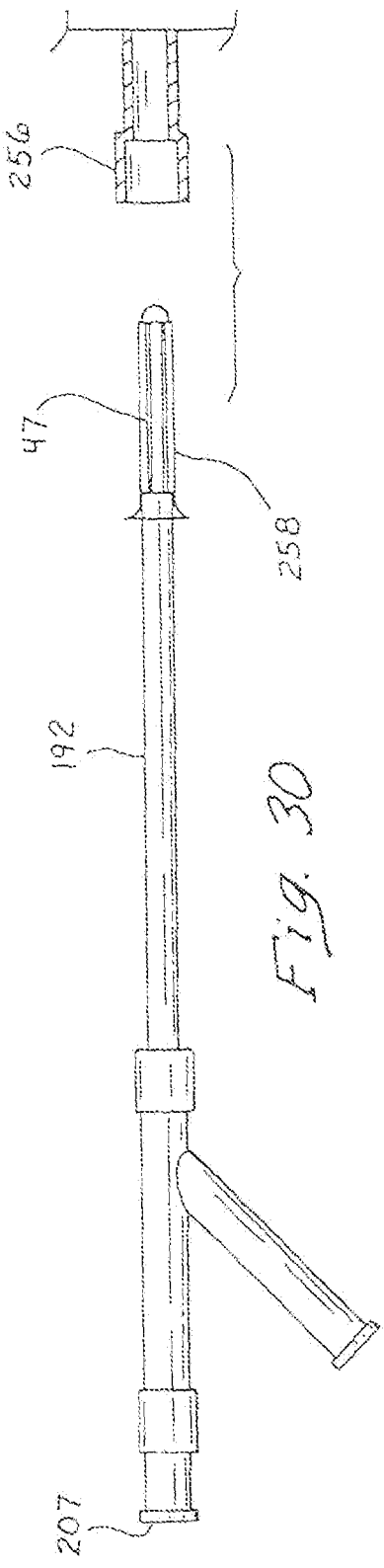

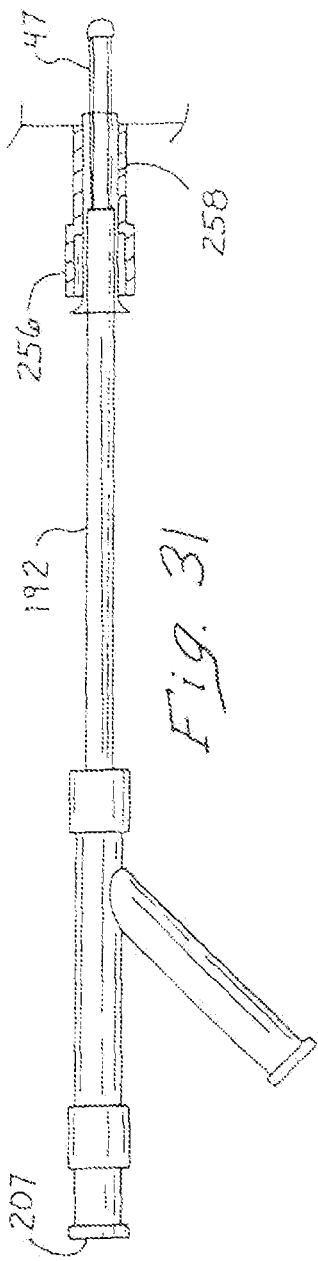
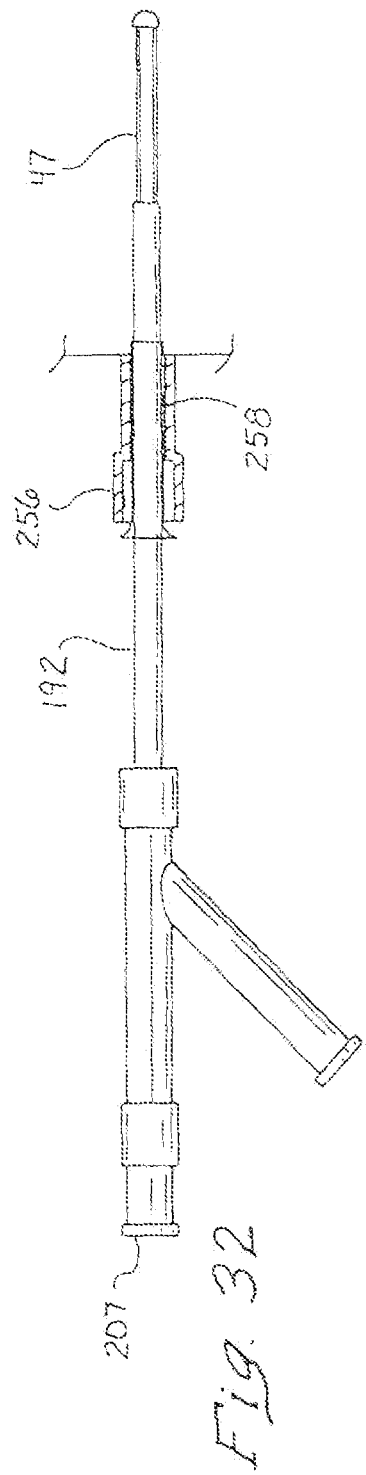
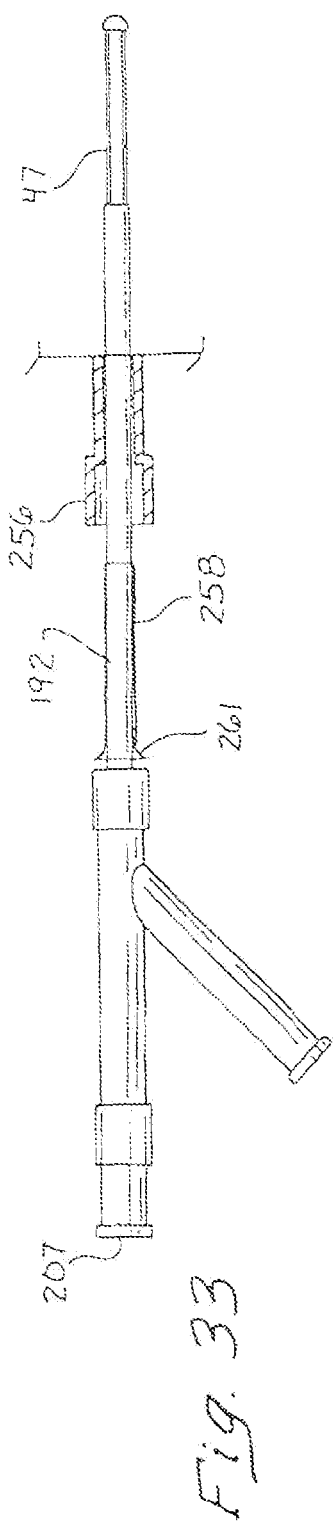

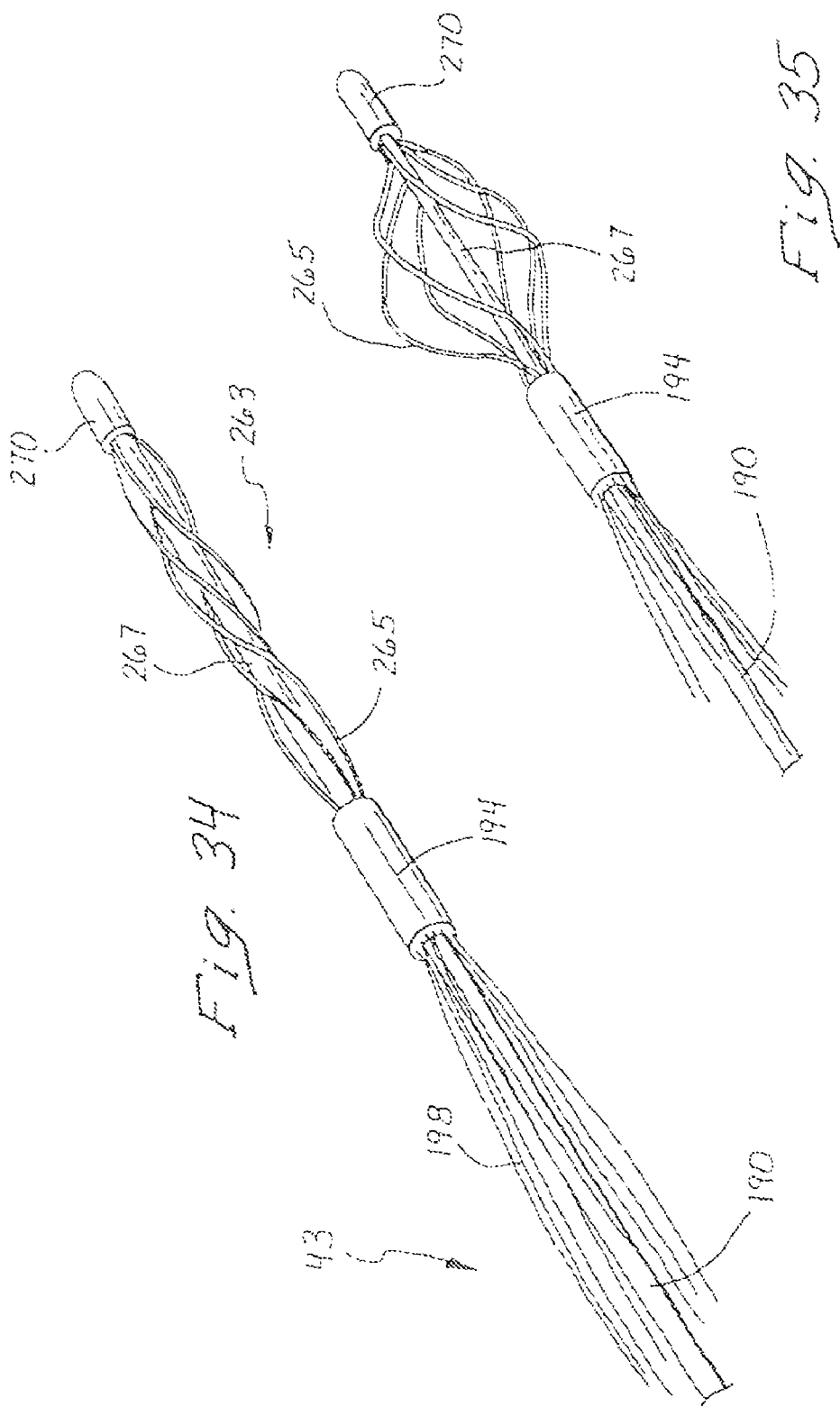

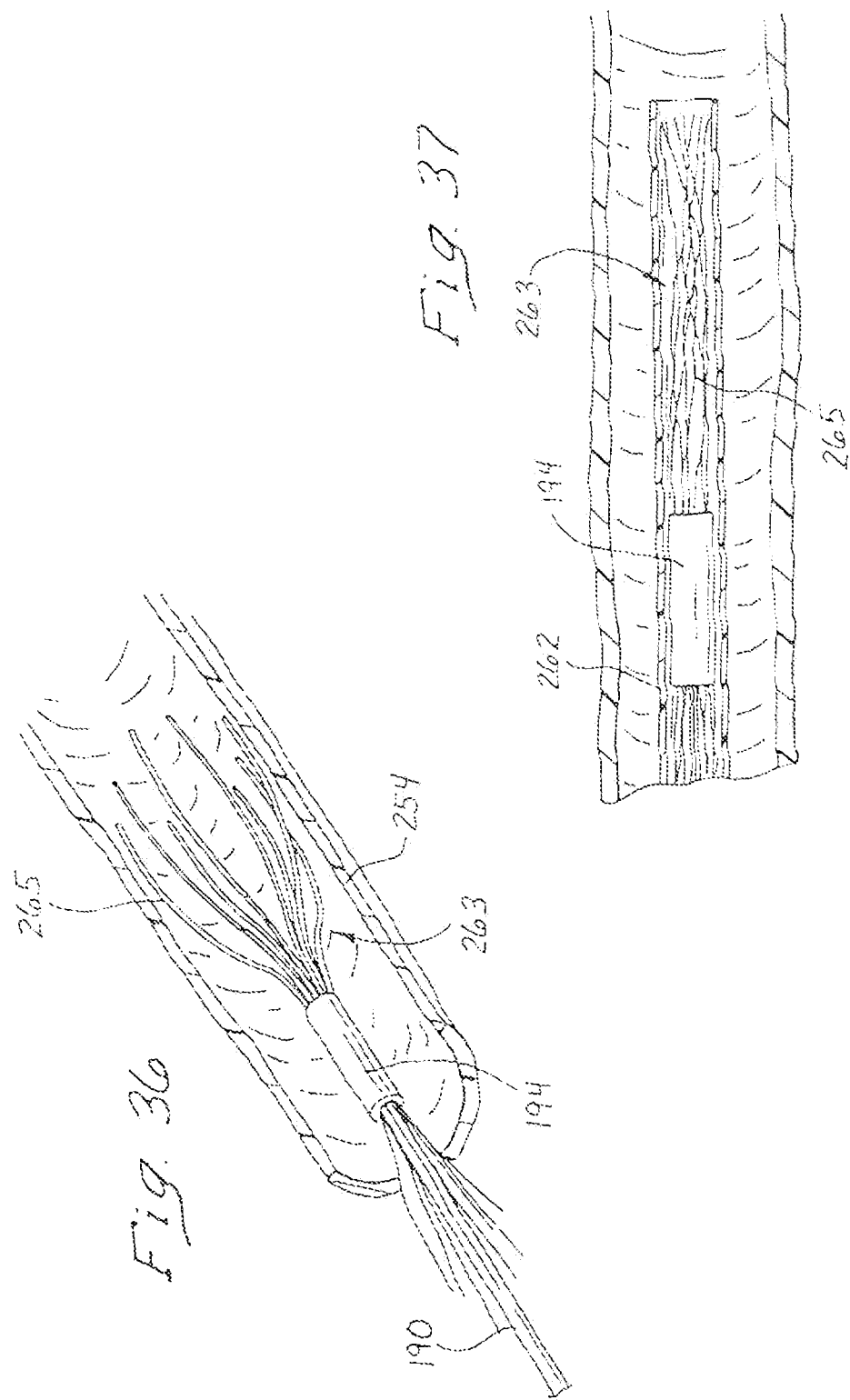

INDWELLING HEAT EXCHANGE CATHETER AND METHOD OF USING SAME

This is a continuation of U.S. patent application Ser. No. 12/794,924, filed Jun. 7, 2010, which is a continuation of U.S. patent application Ser. No. 11/129,980, filed May 16, 2005, now U.S. Pat. No. 7,857,781, which is a continuation of U.S. patent application Ser. No. 09/946,835, filed Sep. 4, 2001, now U.S. Pat. No. 6,893,419, which is a continuation of U.S. patent application Ser. No. 09/133,813, filed Aug. 13, 1998, now U.S. Pat. No. 6,338,727, which is a continuation-in-part of U.S. patent application Ser. No. 09/063,984, filed Apr. 21, 1998, now U.S. Pat. No. 6,126,684, from all of which is priority claimed.

BACKGROUND OF THE INVENTION

1. Field of the Invention

This invention relates generally to apparatus and methods for producing heat exchange with body tissue, and more specifically to methods and apparatus for the hypothermic treatment of a body fluid in a body conduit.

2. Discussion of the Prior Art

Many of the advantages of hypothermia are well known. By way of example, it has been found particularly desirable to lower the temperature of body tissue in order to reduce the metabolism of the body. In stroke, trauma and several other pathological conditions, hypothermia also reduces the permeability of the blood/brain barrier. It inhibits release of damaging neurotransmitters and also inhibits calcium-mediated effects. Hypothermia inhibits brain edema and lowers intracranial pressure.

In the past, hypothermic treatment has been typically addressed systemically, meaning that the overall temperature of the entire body has been lowered to achieve the advantages noted above. This has been particularly desirable in surgical applications where the reduced metabolism has made it possible to more easily accommodate lengthy operative procedures. An example of this systemic approach includes catheters for transferring heat to or from blood flowing within a patient's vessel, as disclosed by Ginsburg in U.S. Pat. No. 5,486,208. A closed loop heat exchange catheter is also disclosed by Saab in U.S. Pat. No. 5,624,392. A cooling device for whole-body hyperthermia that utilizes the circulatory system of the body is known to be more efficient since the entire volume of the body is constantly perfused with the cold fluid at a capillary level.

Likewise, various other means of cooling the body have been tried with cooling blankets, ice water bladder lavages, ice baths, esophageal catheters and their associated methods. All of these devices require a considerable time to cool the body since the primary heat transfer occurs through the skin or the skull. A more efficient body cooling device that can quickly cool and accurately control the body temperature is required.

SUMMARY OF THE INVENTION

A heat exchange catheter and method of operation are included in the present invention. The method is adapted to produce hypothermia or hyperthermia, typically in a selected portion of the body without substantially varying the temperature of the remaining portions of the body. The selected body portion will usually be associated with a body conduit which conveys a body fluid to the selected body portion. Of particular interest are the organs of the body which are commonly nourished and maintained by a flow of blood in the arterial system. For example, a flow of blood is introduced to the brain through the carotid artery. Of course the temperature of this blood is usually at the normal body temperature.

By positioning a heat exchange catheter in the body conduit, heat can be added to or removed from the body fluid to heat or cool the selected body portion. For example, the heat exchange catheter can be disposed in the carotid artery where the arterial blood flowing to the brain can be cooled. The flow of cooled blood to the brain reduces the temperature of the brain thereby resulting in cerebral hypothermia. Importantly, this temperature reduction occurs primarily and selectively in the brain; the remaining portions of the body maintain a generally normal body temperature. In accordance with this method, the selected body portion, such as the brain, can be cooled thereby providing the advantages associated with hypothermia for this body portion. The remainder of the body, such as the portions other than the brain, do not experience the reduction in temperature. Furthermore, the invention is intended to remotely alter temperature in a region other than the point of introduction into the body. This is different than devices intended for systemic temperature control.

Several factors are of interest in effecting heat transfer in a heat exchanger. These factors include, for example, the convection heat transfer coefficient of the two fluids involved in the heat exchange, as well as the thermal conductivity and thickness of the barrier between the two fluids. Other factors include the relative temperature differential between the fluids, as well as the contact area and residence time of heat transfer. The Reynolds number for each fluid stream affects boundary layers, turbulence and laminar flow.

Notwithstanding the need for localized hypothermia, there will always be those procedures which call for systemic hypothermia. Many of the advantages associated with the present invention will greatly facilitate those procedures, for example, by decreasing the number and complexity of operative steps, increasing the heat transfer capacity of the device, and addressing other concerns such as the formation of blood clots.

In one aspect of the invention a catheter is provided with an elongate configuration, a proximal end and a distal end. An outer tube having a first lumen extends between the distal end and proximal end of the catheter, and an inner tube having a second lumen is disposed within the first lumen of the outer tube. Portions of the inner tube define a first flow path extending along the second lumen, while portions of the tubes define a second flow path extending between the first tube and the second tube. A plurality of hollow fibers provide fluid communication between the first and second flow paths, and a heat exchange fluid is disposed in the hollow fibers to cool the fibers.

In another aspect of the invention, a method for making a heat exchange catheter includes the steps of providing first and second tubes having first and second lumens, respectively. A plurality of hollow fibers are connected between a first flow path extending along the second lumen and a second flow path extending along the first lumen outwardly of the second tube. The method further comprises the step of insuring that the second tube is axially or rotationally movable relative to the first tube in order to vary the configuration of the hollow fibers.

In a further aspect of the invention, a method for operating a heat exchange catheter includes the steps of inserting into a body conduit the catheter with an inner tube disposed within an outer tube and defining a first flow path interiorly of the inner tube and second flow path between the inner tube and the outer tube. This inserted catheter also includes a plurality of hollow fibers disposed in fluid communication with the first and second flow paths. The method further includes steps for creating a flow of heat exchange fluid through the first and second flow paths, and moving the inner tube relative to the outer tube to change the profile of the hollow fibers.

In a further aspect of the invention, a heat exchange catheter includes an elongate shaft with first portions defining an inlet lumen and second portions defining an outlet lumen. A first manifold is disposed in fluid communication with the inlet lumen and a second manifold disposed in fluid communication with the outlet lumen. A plurality of hollow fibers are disposed between the manifolds in fluid communication with the inlet and outlet lumens. The catheter is adapted to receive a heat exchange fluid and to direct the heat exchange fluid through the hollow fibers to exchange heat through the hollow fibers.

In still a further aspect of the invention, a catheter is adapted to exchange heat with the body fluid flowing in a first direction through a body conduit. The catheter includes a shaft having an input lumen and an output lumen. A plurality of hollow fibers define a heat exchange region and collectively define an output surface of the heat exchange region. The input lumen of the shaft is coupled to the hollow fibers at a first location while the output lumen of the shaft is coupled to the hollow fibers at a second location disposed in the first direction from the first location.

Another aspect of the invention includes a method for exchanging heat with a body fluid in a body conduit. In this case, a catheter is provided with a plurality of hollow heat exchange fibers extending in fluid communication with an inlet lumen and an outlet lumen of the catheter. The heat exchange fibers collectively define a first cavity in heat transfer relationship with a body fluid in a body conduit.

In an additional aspect of the invention, an operative area of the catheter is sized and configured for disposition in a vessel containing blood. The operative area is adapted to perform a predetermined function, and the blood in the vessel has a tendency to form clots. In this aspect of the invention, the catheter is provided with a snare disposed relative to the operative area and being operable from a proximal end of the catheter to move from a low-profile state facilitating insertion of the catheter, to a high-profile state facilitating the capture of blood clots.

In still a further aspect of the invention, a heat exchange catheter is adapted for cooling the blood of a patient. The catheter includes a heat exchange region with a plurality of fibers each having a hollow configuration. A heat exchange fluid is disposed in the hollow fibers to cool the fibers and a coating is disposed on the outer surface of the fibers to inhibit formation of blood clots.

These and other features and advantages of the invention will be better understood with a description of the preferred embodiments of the invention and reference to the associated drawings.

DESCRIPTION OF THE DRAWINGS

FIG. 1 is side elevation view of a patient lying in a prone position with a heat exchange catheter of the present invention appropriately inserted to facilitate hypothermic treatment of the patient's brain;

FIG. 4 is an enlarged axial cross section view of a plurality of balloons disposed in the heat exchange region of the catheter;

FIG. 5 is a radial cross section view of the catheter taken along lines 5-5 of FIG. 4;

FIG. 6 is a radial cross section view similar to FIG. 5 of a further embodiment of the catheter;

FIG. 7 is a perspective view of a further embodiment of the catheter wherein multiple balloons are provided with a longitudinal configuration;

FIG. 8 is a radial cross section view taken along lines 8-8 of FIG. 7;

FIG. 9 is an axial cross section view taken along lines 9-9 of FIG. 7;

FIG. 10 is a perspective view of the catheter illustrated in FIG. 3 further illustrating structures which can facilitate mixing and heat exchange;

FIG. 10A is a perspective view of an embodiment of the catheter having a distal end with a pigtail configuration;

FIG. 10B is a perspective view of the catheter illustrated in FIG. 10A with the distal end straightened by a stylet 174 to facilitate insertion of the catheter;

FIG. 11 is a schematic view of an embodiment including a heat pipe;

FIG. 12 is a schematic view, partially in section, of a heat pipe adapted for use in the embodiment of FIG. 11;

FIG. 20 is a side elevation view partially in section and illustrating a further embodiment of the catheter of the present invention;

FIG. 21 is a radial cross-section view taken along the lines 21-21 of FIG. 20;

FIG. 22 is an axial cross-section view of the proximal end of the catheter illustrated in FIG. 20;

FIG. 23 is an axial cross-section view of the distal end of a further embodiment illustrating the heat exchange region in a low-profile state;

FIG. 24 is an axial cross-section view similar to FIG. 23 and illustrating the heat exchange region in a high-profile state;

FIGS. 25-27 illustrate a preferred method for manufacturing the heat exchange region of a hollow fiber embodiment of the cavity;

FIG. 25 is a top plan view of a mat formed of the heat exchange fibers;

FIG. 26 is a perspective view illustrating formation of the mat around the distal ends of the concentric tubes;

FIG. 27 is a side elevation view illustrating attachment of the mat assembly to an outer tube of the catheter;

FIG. 29-33 illustrate a method for introducing the catheter of the present invention;

FIG. 29 is a side elevation view illustrating a introducing sheath in a first position removed from the heat exchange region;

FIG. 30 is a side elevation view illustrating the sheath in a second position over the heat exchange region of the catheter;

FIG. 31 is a side elevation view illustrating the catheter and sheath being inserted into an introducer;

FIG. 32 is a side elevation view illustrating the catheter further inserted with the sheath maintained in the introducer;

FIG. 33 is a side elevation view illustrating removal of the sheath to the first position;

FIG. 34 is a perspective view of a further embodiment of the catheter including a distal clot filter in a low-profile state;

FIG. 35 is a perspective view illustrating the catheter of FIG. 34 with the clot filter in a high-profile state;

FIG. 36 is a perspective view of a catheter with a clot filter having free ends and automatically deployable to a high-profile state; and FIG. 37 is a side elevation view of the catheter of FIG. 36 with a sheath maintaining the clot filter in a low-profile state.

DESCRIPTION OF THE PREFERRED EMBODIMENTS AND BEST MODE OF THE INVENTION

Figure 2:
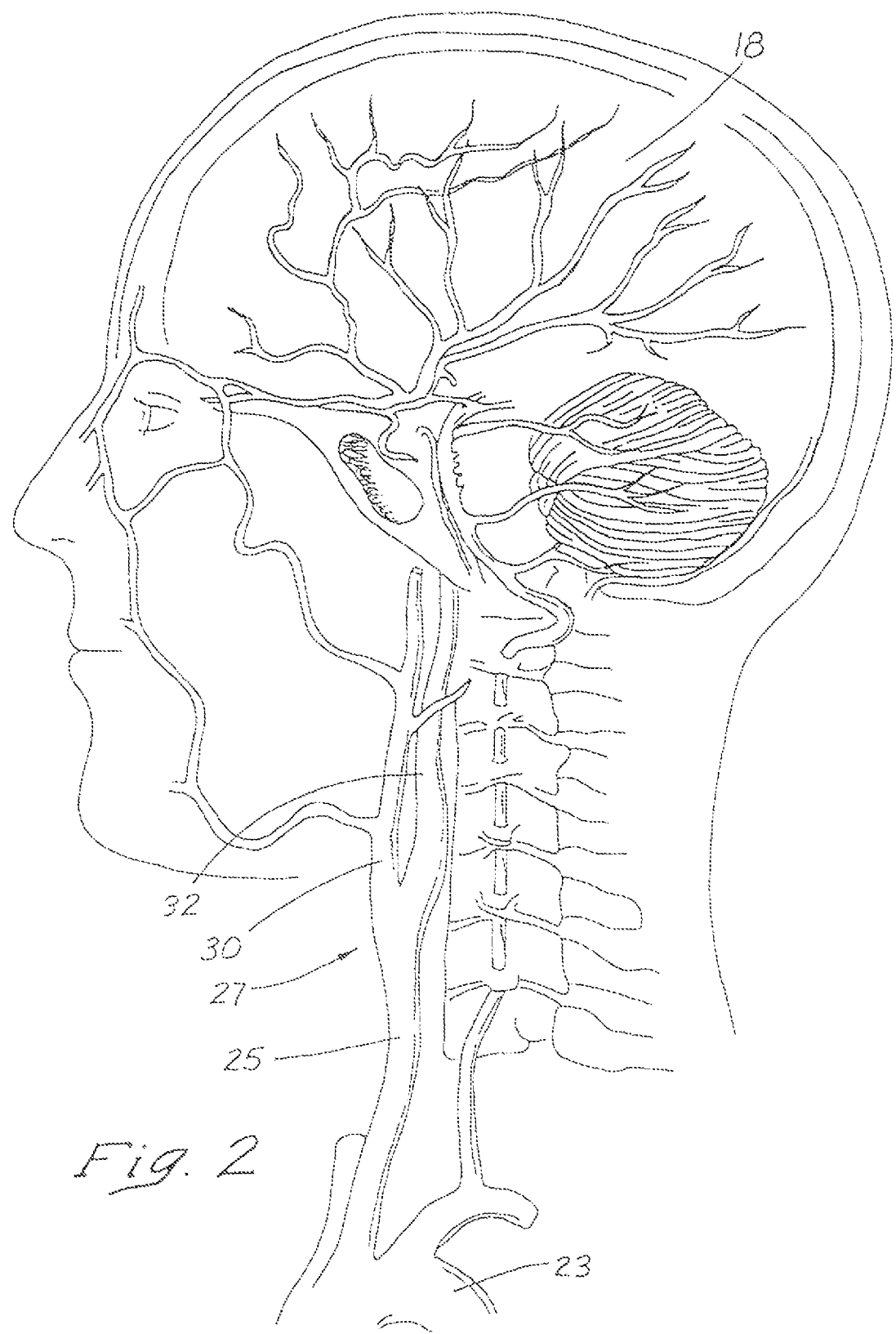
FIG. 2 is an enlarged side elevation view showing the vasculature associated with the patient's head and brain.

A heat exchange catheter is illustrated in FIG. 1 and designated generally by the reference numeral 10. The catheter 10 is operatively disposed with respect to a body 12 of a patient having a groin 14, a head 16, and a brain 18. More specifically, the catheter 10 can be inserted percutaneously through a puncture or surgical cut down at the groin 14, and into the femoral artery 21. Following this initial introduction, the catheter 10 can be moved through the femoral artery 21 and the aortic arch 23, into the common carotid artery 25 best illustrated in FIG. 2. This common carotid artery 25 divides at a carotid branch 27 into an external carotid artery 30, which primarily supplies blood 31 to the face of the patient, and an internal carotid artery 32, which primarily supplies blood to the brain 18 of the patient.

In the concept of this invention, the brain 18 is merely representative of a portion of the body 12 of the patient, and the arteries 21, 25, 30 and 32 are merely representative of conduits which supply a body fluid, such as blood, to a selected portion of the body 12, such as the brain 18. By cooling the body fluid, such as blood 31, in the body conduit, such as the artery 32, the specific body portion, such as the brain 18, can be selectively cooled without significantly affecting the temperature of the remaining portions of the body 12.

Selective hypothermic treatment of the brain 18 is initially of particular interest as it captures the advantages of hypothermia during operative procedures associated with the brain 18 without also capturing the disadvantages of hypothermia with respect to other areas of the body 12. Thus, a surgeon operating to treat an aneurysm in the brain 18, for example, can initially cool the brain 18 in order to facilitate that procedure. This selective hypothermia will be particularly appreciated in those surgical procedures which are primarily directed to the brain 18. Procedures such as stroke, trauma, and other brain related injuries will also benefit up to and during from this selective hypothermia treatment.

Figure 3:
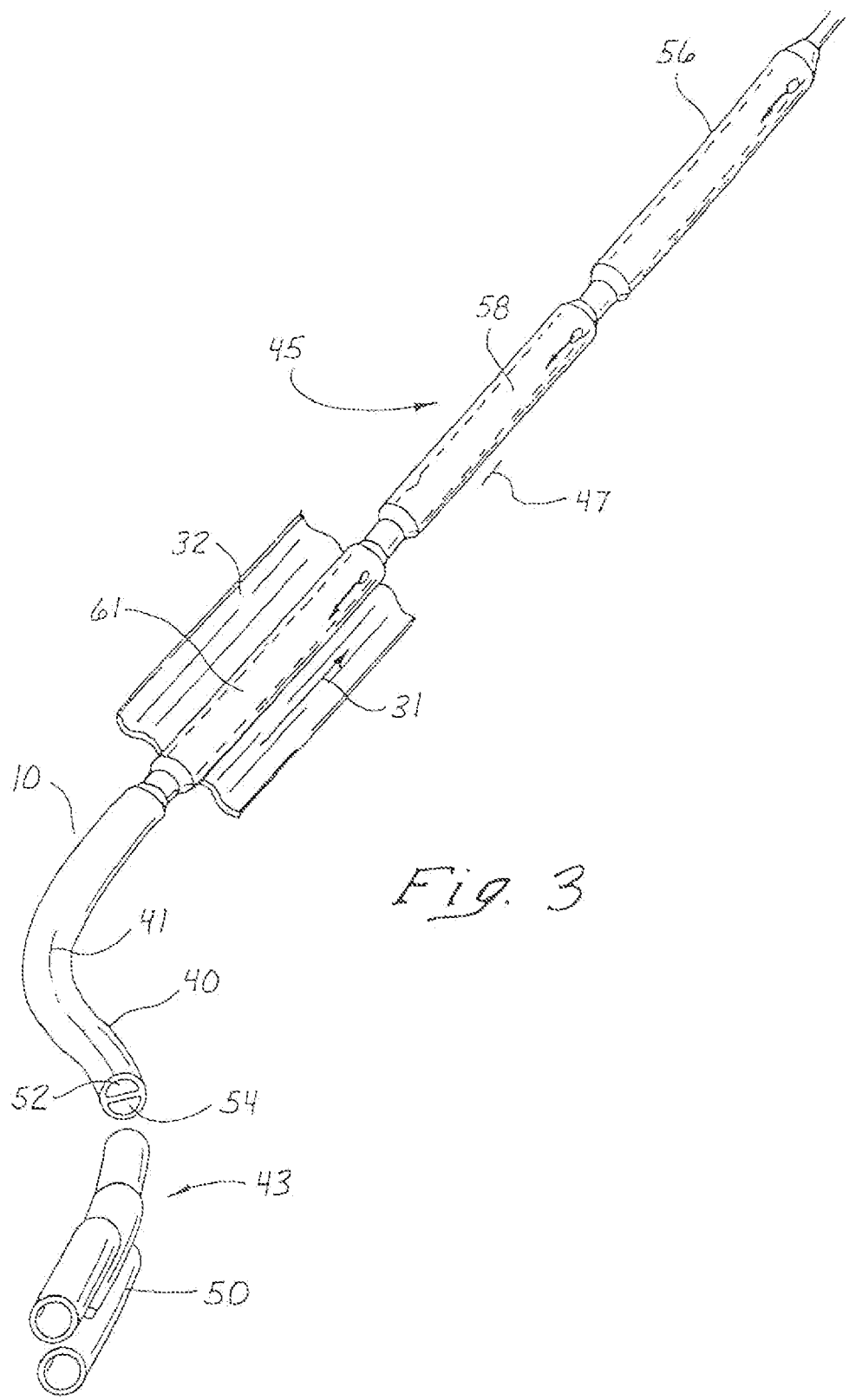
FIG. 3 is a perspective view partially in section of a heat exchange region of the catheter.

A preferred embodiment of the catheter 10 of the present invention is illustrated in FIGS. 3 and 4. From this perspective view, it can be seen that the catheter 10 includes a shaft 40 having an axis 41 which extends between a proximal end 43 and a distal end 45. When operatively disposed, a heat exchange region 47 at the distal end 45 is operatively disposed within the body 12, and a hub 50 at the proximal end 43 is disposed outside of the body 12. Within the shaft 40, a plurality of lumens 52 and 54 extend in fluid communication with the hub 50 and the heat exchange region 47.

A preferred embodiment of the heat exchange region 47 is illustrated in greater detail in FIG. 4 where three balloons 56, 58 and 61 are individually, separately and axially disposed along the shaft 40. It will be appreciated that although the illustrated embodiment includes three balloons, a single balloon or double balloon embodiment may offer further advantages in a particular procedure. All of the balloons 56, 58 and 61 are illustrated to have a significantly larger diameter than the shaft 40. This may not be the case in other embodiments. More specifically, it may be desirable to maximize the dimension of the shaft 40 in order to facilitate flow of the heat exchange fluid. This will also minimize the volume of fluid in the balloon and promote a more rapid heat exchange. In one such embodiment, the diameter of the shaft 40 is in a range between 50 and 90 percent of the diameter of the balloons 56, 58 and 61.

Each of the balloons 56, 58 and 61 can be formed from a piece of sheet material 62, 64 and 66 which is bound or otherwise fixed to the shaft 40 to form a cavity 63, 65 and 67, respectively. An inlet hole 70 provides fluid communication between the lumen 54 and the cavity 63 of the balloon 56. Similar inlet holes 72 and 74 are provided for the balloons 58 and 61. In a like manner, an outlet hole 76 can be formed in the wall of the shaft 40 to provide fluid communication between the lumen 52 and the cavity 63 of the balloon 55. Similar outlet holes 78 and 81 are provided for the balloons 58 and 61, respectively. With this structure, it can be seen that the lumen 54 functions primarily as an inlet lumen for a heat exchange fluid which is illustrated generally as a series of arrows designated by the reference numeral 85.

Initially, the heat exchange fluid 85 is introduced through the hub 50 (FIG. 3) and into the inlet lumen 54. From the lumen 54, the heat exchange fluid 85 passes through the inlet holes 70, 72, 74 and into the respective balloon cavity 63, 65 and 67. The heat exchange fluid 85 then passes into the outlet hole 76, 78, 81 and into the outlet lumen 52 and the hub 50 to regions exterior of the catheter 10.

After the heat exchange fluid 85 is remotely cooled, it is circulated through the balloon cavities 63, 65 and 67 to provide a cold temperature fluid on the inner surface of the sheet materials 62, 64 and 66 which form the walls of the balloons 56, 58 and 61, respectively. With a body fluid, such as blood 31, flowing exteriorly of the balloons 56, 68 and 61, heat transfer occurs across the sheet materials 62, 64 and 66, respectively.

It can be appreciated that this circulation of the heat exchange fluid 85 can be formed with any structure of the shaft 40 which provides two lumens, such as the lumens 52 and 54, each of which can have access to the balloon cavities, such as the cavities 63, 65 and 67. In one embodiment of the shaft 40 illustrated in FIG. 5, a septum 90 is provided which separates the cylindrical shaft 40 into two equally sized lumens 52 and 54. In the embodiment of FIG. 6, the cylindrical shaft 40 is provided with a cylindrical septum 92 which provides the lumen 54 with a circular cross section and the lumen 52 with a moon-shaped cross section. In such an embodiment, the lumen 54 must be defined off-axis from the shaft 40 in order to have access to the balloon cavities, such as the cavity 63.

One of the advantages of a multiple balloon embodiment of the catheter 10 is that the flow and temperature of the heat exchange fluid 85 can be more easily controlled along the entire length of the heat exchange region 47. Realizing that the heat exchange fluid 85 will be coolest prior to entering into a heat exchange with the blood 31, and warmest after that heat exchange, one can advantageously control not only the velocity and volume of flow, but also the direction of flow within each discrete balloons 56, 58 and 61. Another advantage of a multiple balloon design is the ability of the catheter to bend and flex when placed in a curved vasculature. Single balloon designs would be rigid, stiff and inflexible by comparison.

In order to facilitate the maximum heat exchange between the fluid 85 and the blood, it is desirable to provide a balanced flow of the heat exchange fluid 85 along the entire length of the heat exchange region 47. In the embodiment illustrated in FIG. 4, efficient heat transfer is facilitated by countercurrent flow where the heat exchange fluid 85 is directed to flow counter to the flow of the blood 31. To that end, the inlet holes 70, 72 and 74 are positioned distally of the outlet holes 76, 78 and 81, respectively. As the blood 31 flows distally along the outer surface of the catheter 10, this relative position of the inlet holes and outlet holes causes the heat exchange fluid to flow in the opposite direction, proximally in each of the balloons 56, 58 and 61.

The amount of flow within each of the balloons 56, 58 and 61 can also be controlled by the size of the inlet holes 70, 72, 74 and outlet holes 76, 78 and 81. In a preferred embodiment, this flow control is provided solely by the inlet holes 70, 72 and 74; the outlet holes 76, 78 and 81 are sized larger than their respective inlet holes so that they offer little resistance to flow. In this embodiment, the inlet holes 70, 72 and 74 are sized to be progressively smaller from the distal end 45 to the proximal end 43. Thus the hole 70 is larger than the hole 72 which is larger than the hole 74. As a result, the resistance to the flow of heat exchange fluid 85 in the most distal balloon 56 is less than that in the most proximal balloon 61. This ensures that the coolest heat exchange fluid 85 is shared equally among all of the balloons 56, 58 and 61 regardless of their position along the shaft 40. In an embodiment wherein the flow is controlled by the outlet holes 76, 78 and 81, these holes can also be provided with a relatively reduced size from the distal end 45 to the proximal end 43. With any of these structures, a more balanced flow of the heat exchange fluid can be achieved in order to facilitate the highest degree of heat exchange along the entire heat exchange region 47. Alternatively, the flow of heat exchange fluid can also be balanced by providing the holes 76, 78 and 81 with non-circular configurations. For example, these holes may be formed as longitudinal slits extending axially of the catheter.

A further embodiment of the invention is illustrated in FIG. 7 wherein a single sheet of material 101 is used to form separate and distinct individual balloons, two of which are designated by the reference numerals 103 and 105. As opposed to the radial balloons 56, 58 and 61 of the previous embodiment, the balloons 103 and 105 extend axially along the surface of the shaft 40. For example, the balloons 103 and 105 form individual balloon cavities 107 and 110, respectively, which extend from a distal end 112 to a proximal end 114.

This embodiment of the catheter containing the axial balloons 103 and 105 may include a shaft 40 with a slightly different configuration. As best illustrated in FIG. 9, the shaft 40 may include an outer tube 121 having an outer surface to which the sheet material 101 is attached and within which is disposed a distal sealing plug 123. An inner tube 123, which can be disposed coaxially with the outer tube 121, has an inner lumen 127 and defines with the outer tube 121 an outer lumen 130. A pair of inlet holes 132 and 134 provide flow fluid communication between the inner lumen 127 and the balloon cavities 107 and 110, respectively. Similarly, a pair of outlet holes 136 and 138 provide fluid communication between the balloon cavities 107 and 110 and the outer lumen 130, respectively. An inner plug 141 disposed between the inner tube 125 and outer tube 121 to seal the outer lumen 130 between the inlet holes 132, 134 and outlet holes 136, 138. For the reasons previously noted, a preferred embodiment has inlet holes 132, 134 which are disposed distally of and sized smaller than the outlet holes 136, 138, respectively. This orientation will provide countercurrent flow in a catheter 10 which is inserted downstream into an artery such as the carotid artery 25.

Embodiments which are intended to maximize heat transfer will take advantage of the fact that heat exchange is enhanced when either, or both, the body fluid or the heat exchange fluid is provided with well mixed flow. Mixing can be enhanced by providing irregular surfaces next to which either of these fluids flow. For example, with reference to FIG. 4, it will be noted that a spring 150 can be disposed around the shaft 40 inside each of the balloons, such as the balloon 61. In this embodiment, the spring 150 upsets the laminar flow of the heat exchange fluid 85 thereby producing the desired mixing of this fluid. Other structures can be positioned within the cavities formed by the balloons 56, 58 and 61.

Mixing can also be enhanced within the body fluid which flows along the outer surface of the catheter 10. In this case, the multiple radial balloon embodiment illustrated in FIG. 4 is of advantage as each of the balloons 56, 58 and 61 represents a peak and defines with the adjacent balloon a valley along which the blood 31 flows. This series of peaks and valleys also upsets the laminar flow of the body fluid. Mixing of the body fluid can also be enhanced by providing other structures along the outer surface of the sheet material 62, 64 and 66 which form the balloons as well as any exposed areas of the shaft 40 in the heat exchange region 47. By way of example, a multiplicity of granules 145 can be adhered to the outer surface of the radial balloons 56, 58 and 61 or the axial balloons 103 and 105 as illustrated in FIG. 9. Ridges can also be provided along these surfaces.

With some body fluids, it may be desirable to inhibit turbulent flow and facilitate laminar flow. This may be true for example in the case of blood where undesirable hemolysis may occur in response to increased turbulence. Such an embodiment might be particularly desirable for use with radial balloons where an outer balloon 152 would promote laminar flow by reducing the height differential between the peaks and valleys defined by the balloons 56, 58 and 61. This outer balloon 152 is best illustrated in FIG. 10. To further promote laminar flow, the outer surface of any structure in the heat exchange region 47 can be provided with a coating 154, such as a hydrophilic or a hydrophobic coating to modify the boundary layer. Thus the outer surface of the shaft 40 as well as the outer surface of any of the balloons 56, 58, 61, 103, 105 and 152 can be provided with the coating 154. The coating 154 may also include other ingredients providing the catheter 10 with additional advantageous properties. For example, the coating 154 may include an antithrombogenic ingredient such as heparin or aspirin. Such a coating 154 would not only inhibit platelet deposition but also the formation of blood clots.

As previously noted, the characteristics of the heat exchange fluid 85 may also be of importance in a particular heat exchange environment. Although the heat exchange fluid 85 may include various liquids, it is believed that gases may provide the greatest temperature differential with the body fluid. Particularly if this fluid includes blood, gases that are inert or otherwise compatible with the vascular system will be appreciated. Although several inert gases might fulfill these requirements, carbon dioxide is used for the heat exchange fluid 85 in a preferred embodiment of the invention.

A further embodiment of the catheter 10 is contemplated for maximizing the surface area available for heat exchange. As illustrated in FIGS. 10A and 10B, the catheter 10 can be formed with a distal end 45 of the shaft 40 disposed in the natural configuration of a spiral or pigtail 172. The relatively large diameter of the pigtail 172 facilitates heat exchange, but tends to deter from a low profile desire for insertion. Under these circumstances, it may be advantageous to insert the catheter 10 over a stylet or guidewire 174 in order to straighten the pigtail 172 as illustrated in FIG. 10B.

Hyperthermia and hypothermia for selective regions of the body can also be achieved by placing in the body conduit, such as the carotid artery 25, a heat pipe 161 best illustrated in the schematic view of FIG. 11. In this embodiment, the heat pipe 161 includes a distal end 163 and proximal end 165. The distal end 163 is adapted to be placed within the body conduit, such as the carotid artery 25. The proximal end 165 of the heat pipe 161 is adapted to be connected to an external heat sink or cooler, such as a thermoelectric cooler 167 or water jacket 168. A wick structure 170 is provided in the heat pipe 161 to facilitate a flow of heat exchange fluid from the cooler 167 to the distal end 163.

In a process involving the heat pipe 161, illustrated in FIG. 12, the heat exchange fluid is moved from the proximal end 165 of the heat pipe 161 either by gravity or by capillary action of the wick structure 170 to the distal end 163. At the distal end 163 of the heat pipe 161, heat is transferred from the body fluid, such as blood, to the heat exchange fluid in its liquid state. This heat exchange liquid absorbs a heat of vaporization as it passes into a vapor state in the heat pipe 161. The heat exchange fluid in its vapor state creates a pressure gradient between the ends 163 and 165 of the heat pipe 161. This pressure gradient causes the vapor to flow to the cooler 165 where it is condensed giving up its latent heat of vaporization. The heat exchange fluid in its liquid state then passes back through the heat pipe 161 through the wick structure 170 or by gravity. The passive heat exchange system provided by the heat pipe 161 is vacuum-tight and can be operated with a minimum amount of the heat exchange fluid.

Figure 13:
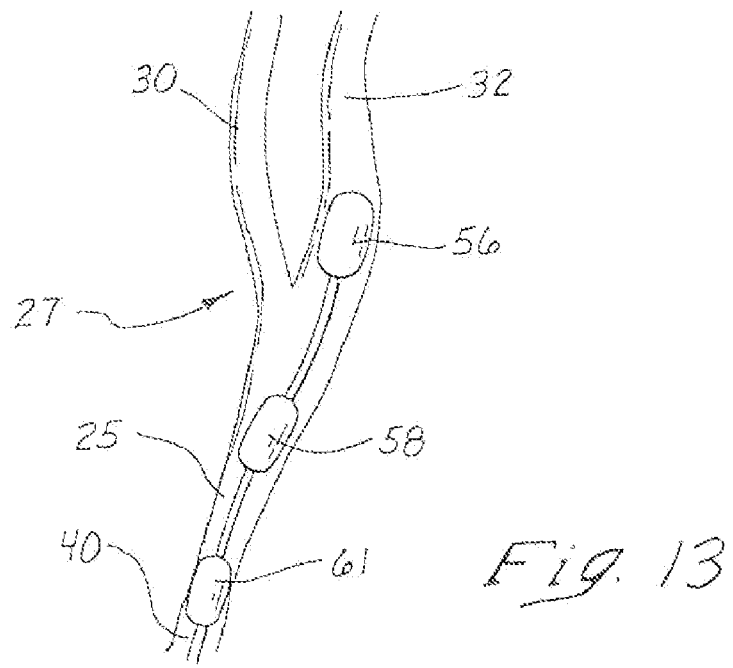
FIG. 13 is a top plan view of carotid artery branch illustrating one method of operation associated with the catheter.

Although the heat exchange catheter 10 will be advantageous in the hyperthermic or hypothermic treatment of any portion of the body 12, it is believed that it will be particularly appreciated in those procedures which can benefit from the hypothermic treatment of the brain 18, such as the treatment of ischemic stroke and/or head trauma. As previously noted in comments directed to FIG. 1, the catheter 10 can be inserted into the femoral artery in the groin 14 and directed through the aortic arch 23 into the common carotid artery 25. As illustrated in FIG. 13, the catheter 10 can then be moved into the region of the arterial branch 27 where it will encounter the external carotid artery 30 and the internal carotid artery 32. Since the external carotid artery 30 is directed primarily to the facial regions, it does not supply a significant amount of blood to the brain 18. In contrast, the internal carotid artery 32 is almost solely responsible for feeding the capillary bed of the brain 18. Based on these considerations, hypothermic treatment of the brain 18 is best addressed by cooling the blood in the internal carotid artery 32 without wasting any of the cooling properties on the external carotid artery 30. In a method associated with one embodiment of the invention, the most distal of the balloons, such as the balloon 56 in FIG. 13 is preferably positioned within the internal carotid artery 32. The more proximal balloons 58 and 61 can be disposed along the common carotid artery 25. This embodiment of the catheter 10 and its associated method will achieve a higher degree of heat transfer within the internal artery 32 than the external artery 30.

Figure 14:
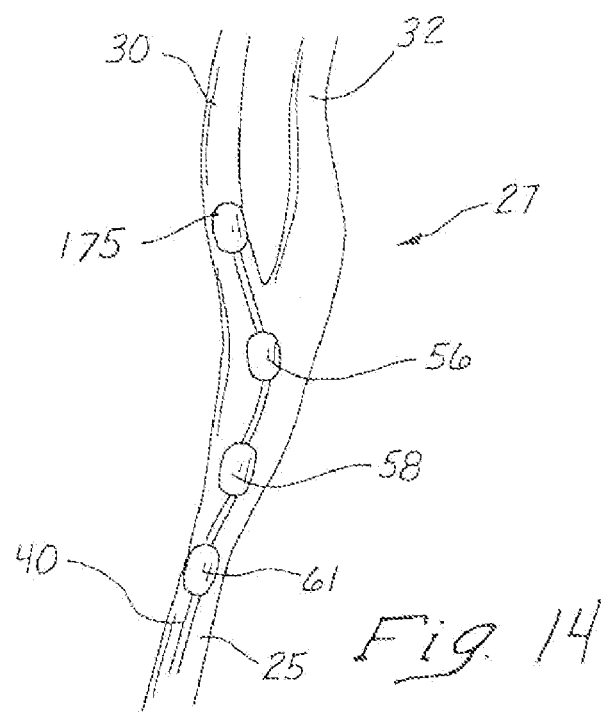
FIG. 14 is a top plan view similar to FIG. 13 and showing a further method of operation with the catheter.

In another embodiment of the catheter 10 best illustrated in FIG. 14, an occlusion balloon 175 is provided distally of the heat exchange region 47. In this embodiment, the occlusion balloon 175 will preferably be inflatable through a separate lumen in the shaft 40. As the catheter 10, approaches the carotid branch 27, the occlusion balloon 175 is directed into the external carotid artery 30 and inflated in order to at least partially occlude that artery. The remaining proximal balloons 56, 58 and 61 in the heat exchange region 47 are left within the common carotid artery 25 to promote heat exchange with the blood flowing to the branch 27. With the external artery 30 at least partially occluded, heat transfer occurs primarily with the blood flowing into the internal carotid artery 32.

Figures 15, 16:
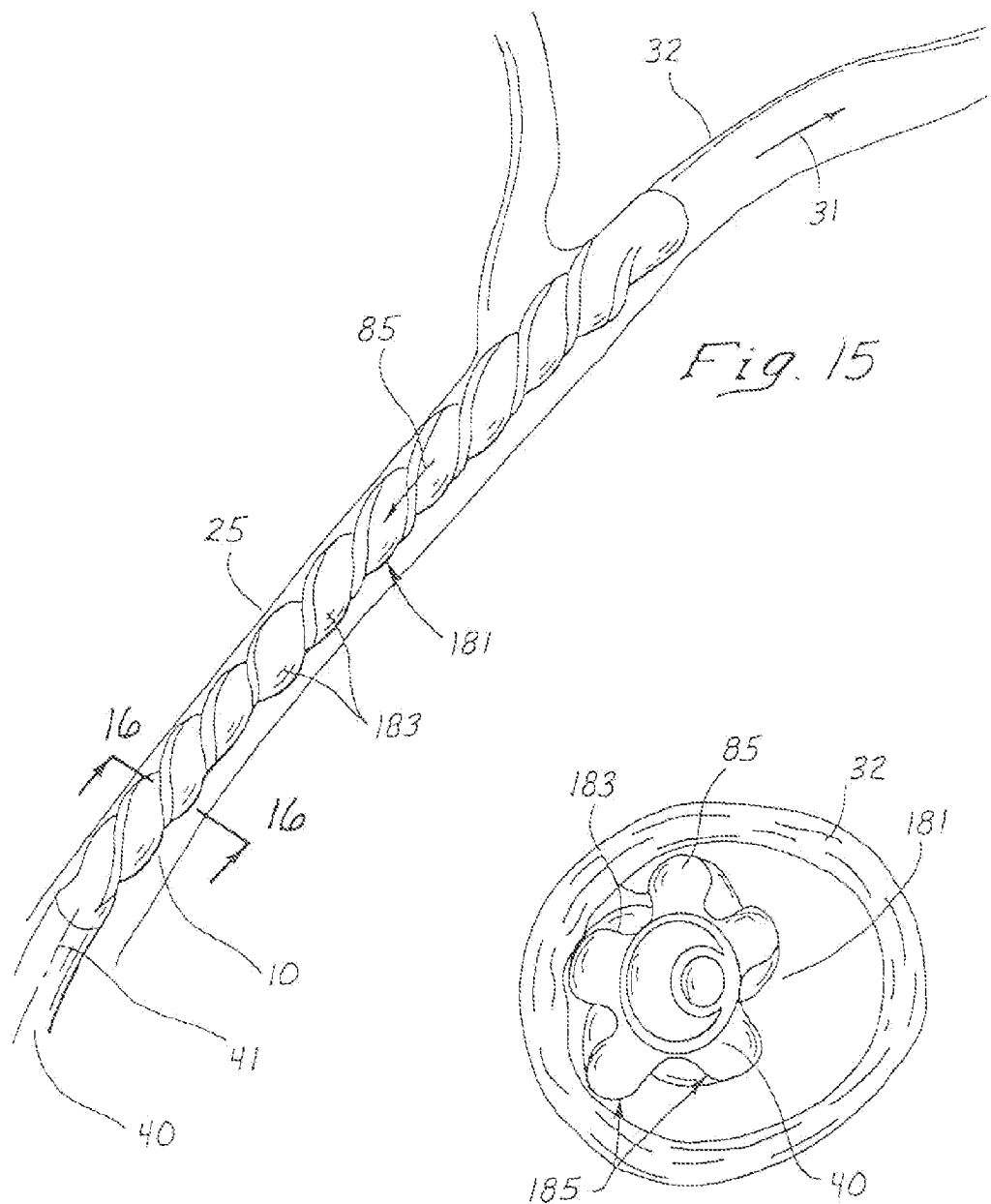
FIG. 15 is a top plan view of the carotid branch similar to FIG. 13 and showing a further method of operating a heat exchange catheter.
FIG. 16 is a radial cross section of the catheter taken along lines 16-16 of FIG. 15.

A further embodiment of the invention is illustrated in FIG. 15 operatively disposed in the common carotid artery 25 and internal carotid artery 32. In this case, the catheter 10 includes a balloon 181 which is attached to the distal end of the shaft 40 and provided with a spiral configuration. More specifically, the balloon 181 may be formed from several individual balloons, as with the embodiment of FIG. 7, for as individual flutes 183 on the single balloon 181. In either case, the separate balloons (such as the balloons 103, 105 of FIG. 7) or the flutes 183 are oriented in a spiral configuration around the axis 41 of the catheter 10. The shaft 40 can be provided with any of the configurations previously discussed such as the eccentric configuration of FIG. 6.

By providing the balloon 181 with a spiral configuration, heat exchange is enhanced by at least two of the factors previously discussed. Notably, the surface area of contact is increased between the blood 31 flowing externally of the balloon 181 and the heat exchange fluid flowing internally of the balloon 181. The spiral configuration also enhances the mixing properties of both the blood 31 and the heat exchange fluid 85.

As noted, the heat exchange fluid 85 may be cooled to a sub-zero temperature. In order to thermally protect the internal lining of the artery 32 from direct contact with the sub-zero coolant, it may be desirable to provide the tips of the flutes 183 with a thicker wall 185, as shown in FIG. 16. This thicker wall 185 might be advantageous in any of the balloon configurations previously discussed, but would appear to be most advantageous in the embodiments of FIGS. 7 and 15 where the contact with the artery 32 tends to be more localized by the longitudinal balloons 103, 105 (FIG. 7) on the spiral flutes 183 (FIG. 15).

Figure 17:
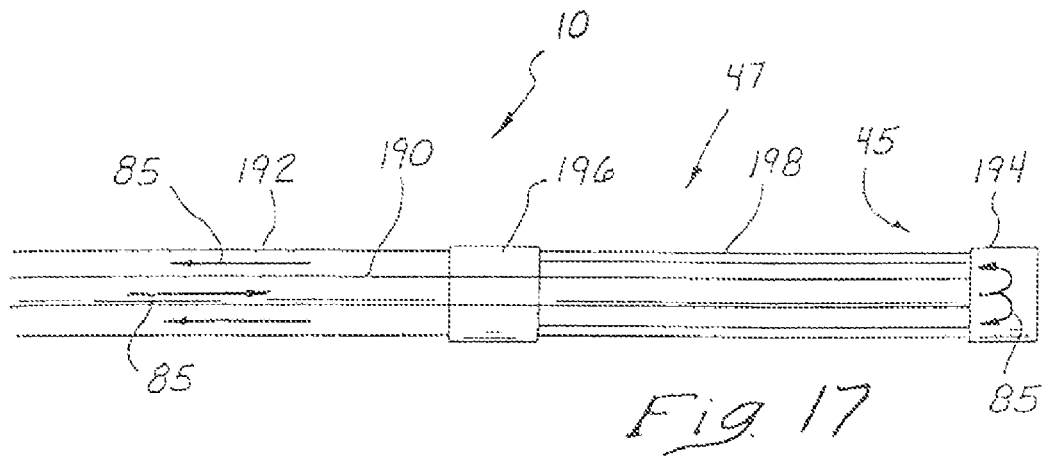
FIG. 17 is an axial cross section view of a further embodiment of the invention including hollow fibers in the heat exchange region.

Still a further embodiment of the invention is illustrated in FIG. 17. In this embodiment, the shaft 40 includes an inner tube 190 disposed within an outer tube 192. These tubes 190, 192 may be concentric and longitudingly movable relative to each other. The tubes 190, 192 terminate respectively in manifolds 194, 196. Between these manifolds 194, 196, a multiplicity of hollow fibers 198 can be disposed at the distal end 45 to define the heat exchange region 47 of the catheter 10. The hollow fibers 198 each include an internal lumen which provides fluid communication between the manifolds 194 and 196. In operation, the heat exchange fluid 85 flows distally along the inner tube 190 into the distal manifold 194. From this manifold 194, the heat exchange fluid 85 flows into the internal lumens of the hollow fibers 198 proximally to the proximal manifold 196. The warmer heat exchange fluid 85 flows proximally from the manifold 196 between the inner tube 190 and outer tube 192.

Preferably, the hollow fibers 198 have a wall thickness that is thin enough to allow maximum heat transfer, yet strong enough to withstand the pressure requirements of the heat exchange fluid 85. The hollow fibers 198 are further adapted to achieve ideal heat transfer by the maximization of both surface area and coolant flow. The smaller the diameter of the fibers 198, the more fibers can be fit into the catheter 10 with a corresponding increase in surface area. As the diameter of the fibers 198 is decreased, however, the resistance to fluid flow increases thus lowering the coolant flow rate. The effect of the inflow and outflow lumens must also be considered in determining the fluid resistance. Ideally, the wall thickness of the hollow fibers 198 is in a range between 0.00025 inches and 0.003 inches. In a preferred embodiment the wall thickness is in a range between 0.00075 inches and 0.002 inches, and ideally 0.00125 inches. The outer diameter of the hollow fibers 198 will typically be between 0.008 inches and 0.035 inches. In a preferred embodiment the outer diameter is in a range between 0.010 inches and 0.018 inches, and ideally 0.015 inches.

It will be noted that the heat exchange fluid 85 flowing in the inner tube 190 is insulated in several respects from the blood stream outside the catheter 10 This flow channel in the inner tube 190 is insulated not only by the wall of the outer tube 192, but also by the coolant returning in the flow channel associated with the outer tube 192. The heat exchange fluid 85 in the inner tube is further insulated by the thickness of the inner tube wall.

In the heat exchange region 47, the wall thicknesses associated with the inner tube 190 and the outer tube 192 is preferably reduced in order to provide additional volume for the hollow fibers 198. With a reduced wall thickness, the inner tube 190 also contributes to the heat exchange occurring in the region 47.

The hollow fibers 198 offer several advantages to this embodiment of the catheter 10. Notably, they provide a very high surface area between the blood 31 and the heat exchange fluid 85. This greatly enhances the heat exchange characteristics of this embodiment. Countercurrent flow can also be maintained further facilitating the heat exchange capabilities of this catheter.

Figure 18:
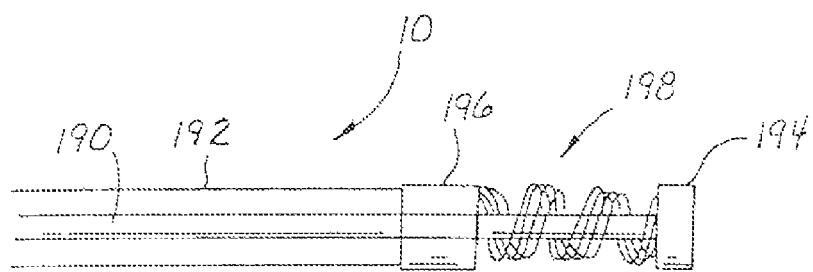
FIG. 18 is a side elevation view similar to FIG. 17 and illustrating the hollow fibers in a compacted configuration.
Figure 19:
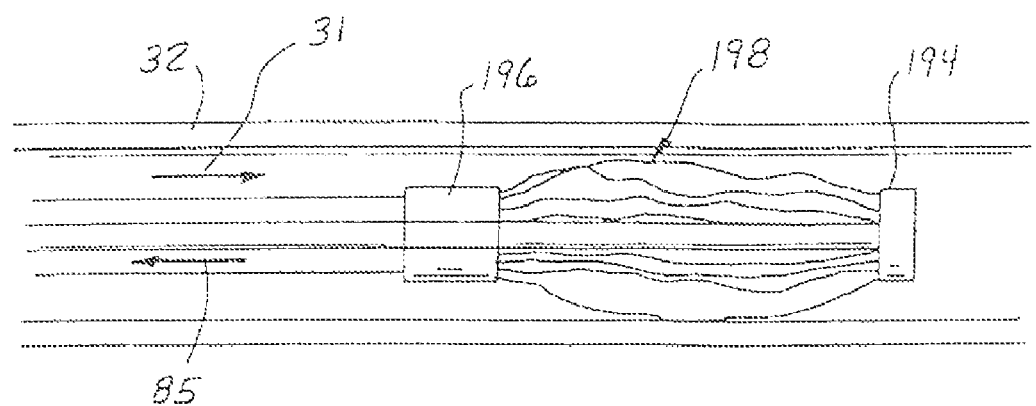
FIG. 19 is art axial cross section view of the catheter of FIG. 17 operatively disposed and configured to permit the hollow fibers to float and undulate within a blood stream.

The hollow fibers 198 can be spiraled as illustrated in FIG. 18 by twisting the inner tube 190 with respect to the outer tube 192. This characteristic can be used to provide a shorter and lower profile heat exchange region 47 in order to facilitate introduction of the catheter 10. A lower profile may also be obtained by separating the manifolds 194 and 196 a distance substantially equal to the length of the fibers 198. This will tend to hold the fibers in a straight, parallel relationship and thereby facilitate introduction of the catheter 10. The spiraled configuration of the hollow fibers 198 can be maintained during heat exchange in order to further increase the heat exchange area per unit length of the catheter 10. Alternatively, the fibers 198 can be positioned to loosely float and undulate between the manifolds 194 and 196 as illustrated in FIG. 19. This characteristic of the fibers 198 will not only provide the increased heat exchange area desired, but also promote mixing within the blood 31.

The fibers 198 will typically be formed of common materials such as polyolefin nylon and polyurethane. The fibers can be coated with a clot-inhibiting material such as heparin. Other materials advantageous for inhibiting the formation of blood clots might include those which form polymer surfaces with 16 or 18 carbon alkyl chains. These materials attract albumin and thereby inhibit clot formation. In a further embodiment, the fibers 198 can be provided with micropores which permit the leaching of such clot inhibiting pharmaceuticals as heparinized saline which could also serve as the heat exchange fluid 85.

The embodiment of FIG. 20 also takes advantage of the significant heat exchange characteristics associated with the hollow fibers 198. In this embodiment, the manifold 194 at the distal end 45 of the catheter 10 includes a potting seal 201 with a distal surface 203. The fibers 198 are held in the potting seal 201 with the lumens of the fibers 198 exposed at the surface 203. The distal end of the inner tube 190 is also held in the potting seal 201 with its lumen exposed at the distal surface 203. In this embodiment, the manifold 194 includes a cap 205 which may have a hemisphere configuration. This cap extends over the distal surface 203 of the potting seal 201 and provides fluid communication between the lumen of the inner tube 190 and the lumens of the hollow fibers 198. This cap 205 may also be constructed of materials and wall thicknesses that insulate the blood vessels from potential contact with a cold catheter tip.

FIG. 21 illustrates in a cross-sectional view a first flow channel 204 which extends along the lumen of the inner tube 190 and a second flow channel 206 which extends along the lumen of the outer tube 192 outwardly of the inner tube 190. As the heat exchange fluid 85 is introduced into the first flow channel 204, its direction is reversed in cap 205 so that the flow of the fluid 85 in the hollow fibers is counter to the flow of the body fluid, such as blood, in the body conduit, such as the artery 32. After moving through the fibers 198, the heat exchange fluid 85 passes along the second flow channel 206 between the inner tube 190 and outer tube 192, and exits the catheter 10 at the proximal end 43.

The embodiment of FIG. 20 also includes a Y-connector 207 disposed at the proximal end 43 of the catheter 10. This connector 207 is shown in greater detail in the enlarged view of FIG. 22. In this view it can be seen that the connector 207 includes a body 210 with screw threads 212 at its distal end and screw threads 214 at its proximal end. At the distal end of the body 210, a screw cap 216 mates with the screw threads 212 to engage an annular flange 218 at the proximal end of the outer tube 192. In this manner, the Y-connector 207 forms a seal with the proximal end of the outer tube 192 and provides fluid communication between the second flow channel 206 and a lumen 221 of the Y-connector 207. A side port 223 communicates with this lumen 221 and provides an exit port for the secondary flow channel 206.

In order to prevent leakage from the lumen 221 at the proximal end 43 of the Y-connector 207, a releasable seal 225 can be formed at the proximal end of the body 210. In the illustrated embodiment, the releasable seal 225 includes a cap 227 which is threaded to register with the threads 214 of the body 210. This cap 227 extends around the proximal end of the body 210 and compresses an elastomeric washer 230 against the body 210 and the outer surface of the inner tube 190. By tightening the cap 227, the washer 230 is compressed to seal the lumen 221. This compression also functions to inhibit, but not necessarily prevent, axial movement between the outer tube 192 and inner tube 190. The releasability of the seal 225 can be appreciated in order to facilitate this relative movement between the tubes 190 and 192 for the reasons previously discussed. This form of a releasable seal 225 is commonly referred to as a Tuohy-Borst seal.

The relative movement between the inner and outer tubes 190 and 192, respectively, will be appreciated in order to provide the tubes 190 and 192 with a first position wherein the fibers 198 have a low profile configuration as illustrated in FIG. 23. The relative movement will also be appreciated in order to provide the tubes 190 and 192 with a second position wherein the hollow fibers 198 form an increased profile as illustrated in FIG. 24. It can be appreciated that this profile will facilitate heat exchange by providing an increased spacing of the individual hollow fibers in the body fluid.

Another feature associated with these two positions is illustrated in FIG. 23 where the inner tube 190 is expanded in thickness at its distal end in order to form a ramp or taper 232. In this embodiment, the taper 232 is annular and extends radially outward with progressive distal positions along the tube 190. As the inner tube 190 is drawn proximally relative to the outer tube 192, the taper 232 is brought into sealing engagement with the proximal end of the hollow fibers 198 and potting seal 201. This effectively seals the distal end of the outer tube 192 against the outer surface of inner tube 190, and prohibits any loss of the heat exchange fluid 85 between the inner and outer tubes 190 and 192 at the distal end 45.

This loss of the heat exchange fluid 85 can also be addressed with a seal tube 234 which can be positioned between the inner and outer tubes 190, 192 and inwardly of the hollow fibers 198. In this embodiment, a distal end 236 of the seal tube 234 is generally coextensive with the distal end of the outer tube 192. The seal tube 234 is preferably provided with an inner diameter greater than the outer diameter of the inner tube 190. As a result, the inner tube 190 is free to move relative to the outer tube 192 to achieve the advantages previously discussed. However, when the inner tube 190 is drawn sufficiently proximal of the outer tube 192, the taper 232 will contact the distal end 236 of the seal tube 234. This effectively forms the seal between the inner and outer tubes 190 and 192, respectively at the distal end of the outer tube 192. With the taper 232 wedged against the seal tube 234, the fibers 198 are maintained in their operative free-floating configuration as illustrated in FIG. 24.

Alternatively, a non-tapered inner tube 190, can be mated with a closely fitted seal tube 234. With very small and controlled differences between the outside diameter of the inner tube 190 and the inside diameter of the seal tube 234, for example 0.0005 to 0.003 inches, an effective seal can be constructed without the taper 232. This embodiment relies on the length of the seal tube 234, the surface tension of the coolant fluid 85, and the small capillary gap to create a resistance greater than the pressure of the coolant fluid during operation. This design does not require the inner tube to be moved a fixed distance relative to the outer tube and does not require a constant tension between the inner and outer tubes to effect a seal.

The seal tube 234 is preferably constructed of polyimide which allows for a precision and constant inner diameter. In addition, polyimide is available in very thin wall thicknesses so that the seal tube 234 will not occupy a significant portion of the annular space which is more appropriately dedicated to the fibers 198.

A method for manufacturing the hollow fiber embodiments of the catheter 10 is illustrated in FIGS. 25-27. In FIG. 25, a planar mat 241 of the hollow fibers 198 is formed with a generally planar configuration. In this mat 241, the fibers 198 are oriented in a generally parallel configuration with angled porting seals 201 and 243 formed at opposite ends of the fibers 198. This fiber mat 241 can be rolled onto the outer surfaces of the inner tube 190 and seal tube 234 as illustrated in FIG. 26. In this step, the potting seal 201 is formed around the distal end of the inner tube 190 while the potting seal 243 is formed around the distal end of the seal tube 234.

By initially forming the fibers 198 into the mat 241, a generally uniform thickness of the mat 241 can be maintained. Rolling the mat 241 onto the tubes 190 and 234 maintains this uniform thickness and also facilitates orientation of the fibers 198 onto the cylindrical tubes 190 and 234. This technique also forms an inwardly spiraling helical bond joint profile that aids in directing the blood flow in order to inhibit clot formation by preventing stagnant blood flow areas at the bond joint. With the potting seals 201 and 243 suitably bonded to the tubes 190 and 234, respectively, the cap 205 can be mounted over the distal end of the fibers 198 as previously discussed. At the proximal end of the fibers 198, the seal tube 234 can be mounted in the distal end of the outer tube 192 as illustrated in FIG. 27.

The seal tube 234 offers some interesting possibilities for the infusion of fluids at the distal end 45 of the catheter 10. Of course, it is always possible to provide an additional lumen within the shaft of the catheter 10. In such an embodiment, the fluid to be infused could be injected into the additional lumen at the proximal end 43 to exit the catheter at the distal end 45. Alternatively, the fluid to be infused might be included in the heat exchange fluid 85. The tolerance between the seal tube 234 and the outer diameter of the inner tube 190 could then be controlled to provide a calibrated leak of the heat exchange fluid 85 at the distal end 45 of the catheter 10. Micro holes might also be drilled into the outer tube 192 or inner tube 190 to provide for a controlled leakage of the infusion fluid.

Figure 28:
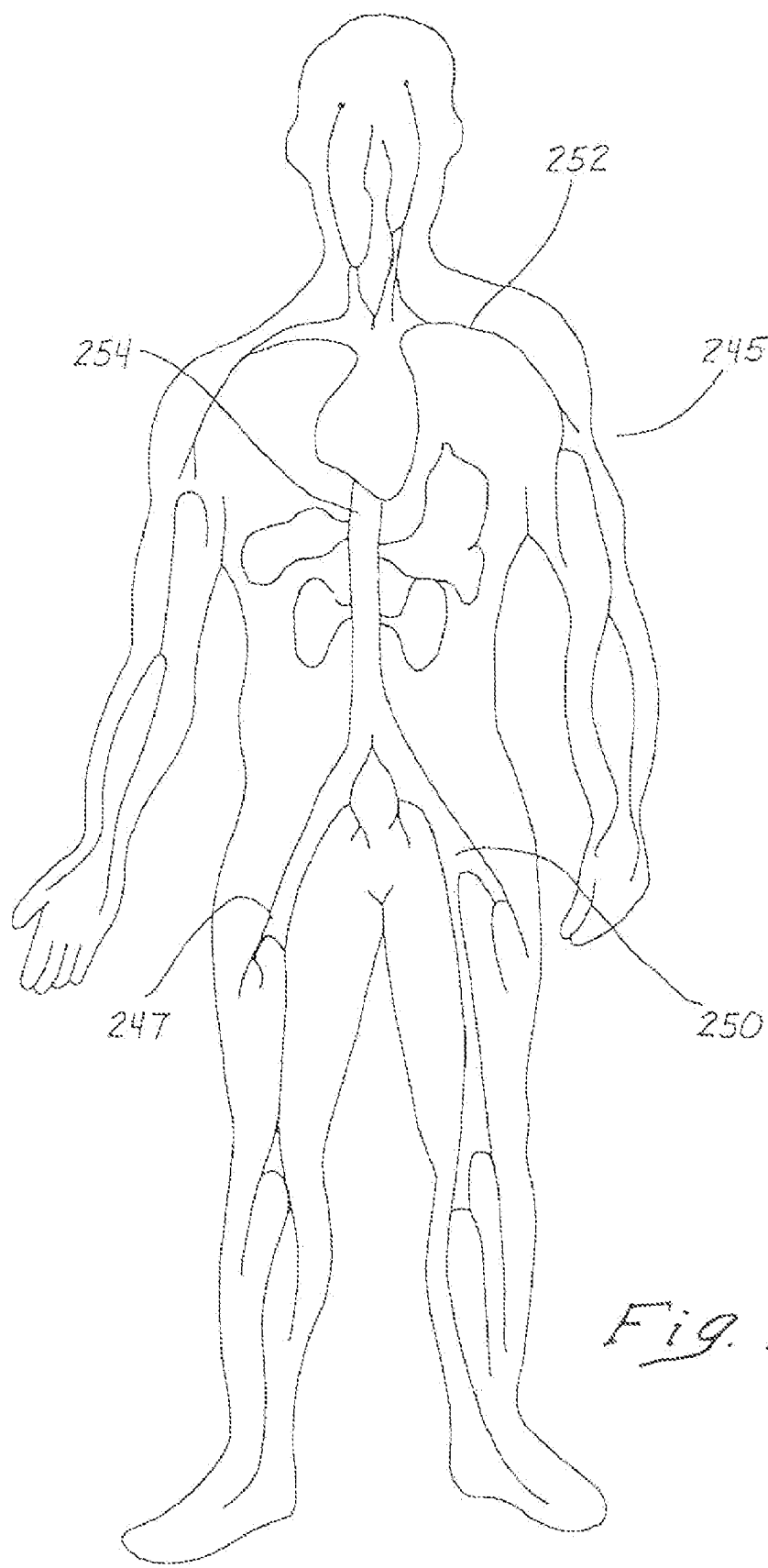
FIG. 28 is a top-plan view of a patient illustrating portions of the blood circulatory system.

Each of the foregoing embodiments of the heat exchange catheter 10 is adapted for use in cooling the entire human body, or perhaps only a portion of the total body. Methods of operation will vary widely depending on the focus of a particular procedure. By way of example, it will be noted with reference to FIG. 28 that the catheter 10 is particularly adapted for cooling blood in a procedure which may involve as many as three of the catheters 10. In FIG. 28, a human body 245 is illustrated along with a portion of the blood circulatory system including a pair of femoral veins 247, 250 and a subclavian vein 252. These veins 247, 250 and 252 all extend into the vena cava 254 of the body 245. In this procedure, separate catheters, such as the heat exchange catheter 10, can be introduced into each of the femoral veins 247, 250 and the subclavian vein 252 with their respective heat exchange regions disposed in the vena cava 254. Alternatively, and preferably, only two such catheters would be introduced from two of the three veins 247, 250 and 252.

A systemic version of the catheter might have a diameter in a range of between 9 and 15 French, and a length of approximately 20 to 80 centimeters long. It is contemplated that this design could conceivably cool the body in several hours. The use of two such catheters inserted into the vena cava 254 as mentioned above could be expected to reduce the time required to cool the body by a factor of 2. It will be appreciated that similar catheters and methods can be used to lower the temperature of blood in the native carotid or in the vertebral circulatory system. The amount of blood heat lost is directly proportional to the temperature differential, the blood velocity and the blood-to-catheter surface area.

Particularly in an operative setting wherein the heat exchange catheter 10 is to be inserted into a blood vessel, a further design feature best illustrated in FIGS. 29-33 will be of particular interest. In these views, an introducer 256 is positioned for percutaneous insertion into a blood vessel such as the femoral vein 250. A sleeve 258 is provided on the catheter 10 and slidable along the outer tube 192 between two positions. The first position is illustrated in FIG. 29 wherein the sleeve 258 is disposed in a spaced relationship with the heat exchange region 47. The second position of the sleeve 258 is illustrated in FIG. 30 where the sleeve 258 covers the heat exchange region 47. In this position the balloons or fibers associated with the region 47 are compressed to a low profile state greatly facilitating introduction of the catheter 10 into the introducer 256. In addition, the covered heat exchange region 47 is stiffened for easier introduction into the introducer 256. The fibers and/or balloons are also protected from the interior surface of the introducer 256. Optionally, a stiffening mandril may be inserted down one or more of the tubes 190, 192 to facilitate introduction of the catheter 10 into the introducer 256.

After this initial insertion, the sleeve 258 remains within the introducer 256 while the remainder of the heat exchange region 47 is moved distally into the conduit as illustrated in FIG. 31. At this point, the sleeve 258 can be removed from the introducer 256 by sliding it proximally to its first position as illustrated in FIG. 33.

This method of introduction is facilitated by providing the sleeve 258 with a generally cylindrical configuration. The diameter of the cylindrical sheath should be less that the inside diameter of the introducer 256. However, at the proximal end of the sheath 258, an annular flange 261 or other enlargement can be provided to ensure that the sheath 258 does not pass beyond the introducer 256.

Another feature associated with the present invention relates to a blood clot basket or snare 263, best illustrated in FIGS. 34 and 35. This snare 263 is preferably positioned downstream of the heat exchange region 47 associated with the catheter 10. It being appreciated that any structure disposed in a blood vessel may tend to generate blood clots, it is the purpose of the snare 263 to capture any such clots. The snare 263 of the preferred embodiment includes a plurality of wires 265 which extend along a shaft 267 with their opposing ends fixed in the manifold 194 and a distal cap 270. The wires 265 in a preferred embodiment are formed of stainless steel or a nickel titanium alloy.

In the illustrated embodiment, the shaft 267 extends to the proximal end 43 of the catheter 10 either through the lumen of the inner tube 190 or alternatively through a second, separate lumen in the inner tube 190. In the former case, a seal would be required at the distal end of the manifold 194 to prevent any leakage of heat exchange fluid 85 around the shaft 267.

In either case, the shaft 267 is free to move relative to the concentric tubes 190 and 192. When the shaft 267 is moved relatively distally, the snare wires 265 are provided with a generally low profile. When the shaft 267 is moved relatively proximally, the wires 265 deploy to provide the snare with an enlarged high-profile configuration as illustrated in FIG. 35.

In a further embodiment of the snare 263, the wires 265 are connected to the manifold 194 and extend to distal ends which are unattached or free. The wires 265 in this embodiment, best illustrated in FIG. 36, are bent to a deployed enlarged configuration. With such an embodiment, insertion is facilitated by providing a delivery sheath which is movable to maintain the wires 265 in a low-profile state. Once the catheter 10 is in place, the sheath 262 can be removed thereby permitting the wires 265 to automatically expand to their enlarged high-profile state.

With respect to the forgoing disclosure as a whole, it will be apparent that many variations from these preferred embodiments will now be apparent to those skilled in the art. For example, with respect to the balloon embodiments previously discussed, it will be appreciated that the advantages of this invention can be derived with only a single balloon. On the other hand, there seem to be several advantages associated with multiple balloon embodiments. Notably, a more even and balanced transfer of heat exchange can be achieved with multiple balloons. In addition, there appears to be better mixing with respect to both the blood 31 as well as the heat exchange fluid 85. Multiple balloons also provide an increased surface area relative to single balloon embodiments. Furthermore, the overall flexibility of the catheter 10 is enhanced with multiple balloons separated by interruptions which provide natural flex points for the catheter. When the balloons experience the high perfusion pressure, they become more stiff. The reduced diameter interruptions provide for increased flexibility at these joints.

Additional flexibility can be derived by providing the shaft 40 with variable stiffness. This variability can be produced by different materials forming the shaft 40 along its length or alternatively, tapering or otherwise varying the diameter of the shaft 40. For example, the shaft 40 can be progressively tapered from its proximal end 43 to its distal end 45 in order to provide a softer and more flexible heat exchange region 47.

In any of the foregoing embodiments of the catheter 10, the inner tube 190 can be provided with a central lumen facilitating introduction over a guidewire and providing a capability for the infusion of fluids through the catheter 10.

With the intent of maximizing heat transfer with the body fluid in a conduit feeding a specific region of the body, any of the factors previously noted can be addressed to provide structural modifications to the foregoing embodiments. Of course changes in the material or size of any of the structural elements described can be varied to achieve various heat exchange properties. Realizing the many changes which might be contemplated, one is cautioned not to limit this concept only to the specific embodiments illustrated and disclosed, but rather to determine the scope of the invention with reference to the following claims.

The invention claimed is:

1. Heat exchange catheter comprising:
   catheter body; and
   at least one heat exchange element distally associated with the catheter body and having either or both of: exterior structure that disrupts laminar flow of blood therealong, and interior structure that disrupts laminar flow of heat exchange fluid therealong, heat exchange fluid flowing through the heat exchange element but not into a patient in which the catheter is disposed to exchange heat with a patient's body;
   wherein at least one heat exchange element is externally fluted in a spiral configuration along at least a segment thereof, wherein body fluid laterally outward of the heat exchange element cannot flow between the heat exchange element and a long axis defined by the spiral configuration of the heat exchange element.

2. The catheter of claim 1, comprising plural heat exchange elements axially arranged with respect to each other.

3. The catheter of claim 1, wherein the catheter is provided with distal metal structure.

4. The catheter of claim 1, comprising an anti-thrombogenic coating on at least a portion of the catheter.

5. The catheter of claim 1, wherein the heat exchange element externally fluted in a spiral configuration has exterior structure that disrupts laminar flow of blood therealong.

6. The catheter of claim 1, wherein at least one heat exchange element has interior structure that disrupts laminar flow of heat exchange fluid therealong.

7. The catheter of claim 5, wherein the heat exchange element externally fluted in a spiral configuration has interior structure that disrupts laminar flow of heat exchange fluid therealong.

8. Apparatus comprising:
   a catheter body having at least one heat exchange fluid lumen; and
   at least one heat exchange element communicating with the lumen such that heat exchange fluid is through the heat exchange element to exchange heat with blood of a patient when the heat exchange element is positioned in bloodstream of the patient, the heat exchange fluid not entering the bloodstream, wherein the heat exchange element(s) are configured to enhance heat exchange by being configured with at least one irregular surface next to which blood and/or heat exchange fluid flows;

wherein a single heat exchange element is formed with plural spiral flutes.

9. The apparatus of claim 8, wherein the irregular surface is spiral-shaped.

10. The apparatus of claim 8, wherein the irregular surface is established by structure defining peaks and valleys to upset laminar flow of fluid.

11. The apparatus of claim 8, wherein the irregular surface is established by ridges.

12. The apparatus of claim 8, wherein tips of flutes on the heat exchange element define walls having a thickness greater than a thickness of other portions of the catheter.

13. The apparatus of claim 8, wherein first and second heat exchange elements are separated from each other by a flex region.

14. The apparatus of claim 8, wherein the body has a stiffness at a first location of the body that is different from a stiffness at a second location of the body.

15. The apparatus of claim 14, wherein the first location has a first diameter and the second location has a second diameter different from the first location.

16. The apparatus of claim 8, wherein body fluid laterally outward of the heat exchange element cannot flow between the heat exchange element and a long axis defined by the spiral flutes.

17. The apparatus of claim 8, comprising plural heat exchange elements axially arranged along the body such that the catheter can bend and flex when placed in a curved vasculature and is not as rigid, stiff and inflexible by comparison to a single heat exchange element catheter.

18. The apparatus of claim 8, comprising an anti-thrombogenic coating on at least a portion of the catheter.

19. The apparatus of claim 17, wherein the heat exchange elements extend axially along a surface of the body.

20. The apparatus of claim 8, comprising a hydrophilic or hydrophobic coating on at least a portion of the catheter.

21. The apparatus of claim 8, wherein a pressure gradient is established from a first end of the heat exchange element to a second end thereof.

22. Apparatus comprising:

a catheter body having at least one heat exchange fluid lumen; and at least one heat exchange element communicating with the lumen such that heat exchange fluid is through the heat exchange element to exchange heat with blood of a patient when the heat exchange element is positioned in bloodstream of the patient, the heat exchange fluid not entering the bloodstream, wherein the heat exchange element(s) defines structure to upset laminar flow of fluid therealong;

wherein at least one heat exchange element is externally fluted in a helical configuration along at least a segment thereof, wherein body fluid laterally outward of the heat exchange cannot pass to a long axis defined by the spiral configuration of the heat exchange element.

23. The apparatus of claim 22, wherein the structure includes at least one irregular surface next to which blood and/or heat exchange fluid flows.

24. The apparatus of claim 23, wherein the irregular surface is spiral-shaped.

25. The apparatus of claim 22, wherein the structure is established by peaks and valleys.

26. The apparatus of claim 22, wherein the structure is established by ridges.

27. The apparatus of claim 22, wherein a single heat exchange element is externally fluted in a spiral configuration along at least a segment thereof.

28. The apparatus of claim 22, wherein tips of flutes on the heat exchange element define walls having a thickness greater than a thickness of other portions of the catheter.

29. The apparatus of claim 22, comprising first and second heat exchange elements separated from each other by a flex region.

30. The apparatus of claim 22, wherein the body has a stiffness at a first location of the body that is different from a stiffness at a second location of the body.

31. The apparatus of claim 30, wherein the first location has a first diameter and the second location has a second diameter different from the first location.

32. The apparatus of claim 22, comprising plural heat exchange elements axially arranged along the body such that the catheter can bend and flex when placed in a curved vasculature and is not as rigid, stiff and inflexible by comparison to a single heat exchange element catheter.

33. The apparatus of claim 22, comprising an anti-thrombogenic coating on at least a portion of the catheter.

34. The apparatus of claim 22, comprising a hydrophilic or hydrophobic coating on at least a portion of the catheter.

35. The apparatus of claim 22, wherein a pressure gradient is established from a first end of the heat exchange element to a second end thereof.

* * * * *